US007931698B2

(12) United States Patent
Simonet et al.

(10) Patent No.: US 7,931,698 B2
(45) Date of Patent: Apr. 26, 2011

(54) READY-TO-USE COMPOSITION FOR OXIDATION DYEING OF KERATIN FIBERS COMPRISING AT LEAST ONE FATTY SUBSTANCE, AT LEAST ONE THICKENER, AT LEAST ONE DYE PRECURSOR, AT LEAST ONE OXIDIZING AGENT, AND AT LEAST ONE ALKALINE AGENT, AND PROCESS AND KITS THEREWITH

(75) Inventors: Frédéric Simonet, Clichy (FR); Luc Nicolas-Morgantini, Rully (FR); Irène Fonseca, Montigy les Cormeilles (FR); Leïla Hercouet, Neuilly Plaisance (FR); Marie-Pascale Audousset, Asnieres (FR); Jean-Marc Ascione, Paris (FR); Florence Laurent, Bois Colombes (FR)

(73) Assignee: L'Oreal S.A., Paris (FR)

(*) Notice: Subject to any disclaimer, the term of this patent is extended or adjusted under 35 U.S.C. 154(b) by 0 days.

(21) Appl. No.: 12/642,480

(22) Filed: Dec. 18, 2009

(65) Prior Publication Data
US 2010/0154140 A1 Jun. 24, 2010

Related U.S. Application Data

(60) Provisional application No. 61/150,099, filed on Feb. 5, 2009.

(30) Foreign Application Priority Data

Dec. 19, 2008 (FR) ..................................... 08 07321

(51) Int. Cl.
*A61Q 5/10* (2006.01)
(52) U.S. Cl. ............. 8/405; 8/406; 8/410; 8/411; 8/421; 8/435; 8/552; 8/557; 8/580; 8/604
(58) Field of Classification Search .............. 8/405, 406, 8/410, 411, 421, 435, 552, 557, 580, 604
See application file for complete search history.

(56) References Cited

U.S. PATENT DOCUMENTS

| 3,100,739 A | 8/1963 | Kaiser et al. |
| 3,369,970 A | 2/1968 | McLaughlin et al. |
| 3,629,330 A | 12/1971 | Brody et al. |
| 3,861,868 A | 1/1975 | Milbrada |
| 4,138,478 A | 2/1979 | Reese et al. |
| 4,170,637 A | 10/1979 | Pum |
| 4,226,851 A | 10/1980 | Sompayrac |
| 4,357,141 A | 11/1982 | Grollier et al. |
| 4,366,099 A | 12/1982 | Gaetani et al. |
| 4,488,564 A | 12/1984 | Grollier et al. |
| 4,725,282 A | 2/1988 | Hoch et al. |
| 4,845,293 A | 7/1989 | Junino et al. |
| 5,021,066 A | 6/1991 | Aeby et al. |
| 5,259,849 A | 11/1993 | Grollier et al. |
| 5,364,414 A | 11/1994 | Lang et al. |
| 5,817,155 A | 10/1998 | Yasuda et al. |
| 6,010,541 A | 1/2000 | De La Mettrie |
| 6,074,439 A | 6/2000 | De La Mettrie et al. |
| 6,129,770 A | 10/2000 | Deutz et al. |
| 6,156,713 A | 12/2000 | Chopra et al. |
| 6,165,444 A | 12/2000 | Dubief et al. |
| 6,190,421 B1 | 2/2001 | Rondeau et al. |
| 6,206,935 B1 | 3/2001 | Onitsuka et al. |
| 6,238,653 B1 | 5/2001 | Narasimhan et al. |
| 6,251,378 B1 | 6/2001 | Laurent et al. |
| 6,260,556 B1 | 7/2001 | Legrand et al. |
| 6,277,154 B1 | 8/2001 | Lorenz |
| 6,277,155 B1 | 8/2001 | De La Mettrie et al. |
| 6,365,136 B1 | 4/2002 | Lauscher et al. |
| 6,423,100 B1 | 7/2002 | Lang et al. |
| 6,447,552 B1 | 9/2002 | Golinski |
| 6,645,258 B2 | 11/2003 | Vidal et al. |
| 6,660,045 B1 | 12/2003 | Hoeffkes et al. |
| 6,695,887 B2 | 2/2004 | Cottard et al. |
| 6,800,098 B1 | 10/2004 | Allard et al. |
| 7,135,046 B2 | 11/2006 | Audousset |
| 7,153,331 B2 | 12/2006 | Desenne et al. |
| 7,217,298 B2 | 5/2007 | Legrand et al. |

(Continued)

FOREIGN PATENT DOCUMENTS

CA 1 268 421 5/1990

(Continued)

OTHER PUBLICATIONS

French Search Report for FR 0807321, dated Aug. 5, 2009.
English language abstract of DE 10 2006 012 575 A1, Henkel KGaA, Feb. 2007.
Copending U.S. Appl. No. 12/339,753, filed Dec. 19, 2008.
Copending U.S. Appl. No. 12/339,781, filed Dec. 19, 2008.
Copending U.S. Appl. No. 12/339,820, filed Dec. 19, 2008.
Copending U.S. Appl. No. 12/642,412, filed Dec. 18, 2009.
Copending U.S. Appl. No. 12/642,451, filed Dec. 18, 2009.

(Continued)

*Primary Examiner* — Eisa B Elhilo
(74) *Attorney, Agent, or Firm* — Finnegan, Henderson, Farabow, Garrett & Dunner

(57) ABSTRACT

Provided is a ready-to-use composition for the oxidation dyeing of keratin fibers, and for example of human keratin fibers such as the hair, comprising, A) at least one fatty substance other than fatty acids present in the ready-to-use composition in an amount of greater than or equal to 25% by weight relative to the total weight of the ready-to-use composition, B) at least one polymeric thickener, C) at least one dye precursor, D) at least one oxidizing agent and E) at least one alkaline agent wherein at least one of the at least one alkaline agent is an organic amine. Also provided is a method of dyeing keratin fibers, comprising applying the ready-to-use composition to the keratin fibers for a sufficient time to develop the desired coloration.

24 Claims, No Drawings

U.S. PATENT DOCUMENTS

| | | | |
|---|---|---|---|
| 7,285,137 B2 | 10/2007 | Vidal et al. |
| 7,442,215 B2 | 10/2008 | Audousset et al. |
| 7,458,993 B2 | 12/2008 | Cottard et al. |
| 7,494,513 B2 | 2/2009 | Kravtchenko et al. |
| 7,575,605 B2 | 8/2009 | Legrand |
| 7,651,533 B2 | 1/2010 | Legrand |
| 7,651,536 B2 | 1/2010 | Cottard et al. |
| 7,766,977 B2 | 8/2010 | Cottard et al. |
| 7,799,095 B2 | 9/2010 | Mario et al. |
| 2003/0190297 A1 | 10/2003 | Narasimhan et al. |
| 2003/0226217 A1 | 12/2003 | Bowes et al. |
| 2004/0103488 A1 | 6/2004 | Yamashita et al. |
| 2004/0105830 A1 | 6/2004 | Boswell et al. |
| 2004/0181883 A1 | 9/2004 | Legrand et al. |
| 2004/0226110 A1 | 11/2004 | LeGrand |
| 2004/0234700 A1 | 11/2004 | Legrand et al. |
| 2005/0129652 A1 | 6/2005 | Keller et al. |
| 2005/0165705 A1 | 7/2005 | Lauper et al. |
| 2005/0196367 A1 | 9/2005 | Ohta et al. |
| 2006/0042023 A1 | 3/2006 | Machida |
| 2006/0075580 A1 | 4/2006 | Chan et al. |
| 2006/0137111 A1 | 6/2006 | Au et al. |
| 2006/0242773 A1 | 11/2006 | Kravtchenko et al. |
| 2006/0260071 A1 | 11/2006 | Legrand |
| 2006/0265817 A1* | 11/2006 | Legrand ............... 8/405 |
| 2007/0006397 A1 | 1/2007 | Schmenger et al. |
| 2007/0033743 A1 | 2/2007 | Kravtchenko |
| 2007/0104672 A1 | 5/2007 | Decoster et al. |
| 2007/0169285 A1 | 7/2007 | Narasimhan et al. |
| 2007/0275927 A1 | 11/2007 | Philippe |
| 2007/0277331 A1 | 12/2007 | Goldstein et al. |
| 2008/0016627 A1 | 1/2008 | Cottard et al. |
| 2008/0071092 A1 | 3/2008 | Vidal et al. |
| 2008/0229512 A1 | 9/2008 | Syed et al. |
| 2008/0256724 A1 | 10/2008 | Bolton et al. |
| 2009/0007347 A1 | 1/2009 | Cottard et al. |
| 2009/0060855 A1 | 3/2009 | Boche et al. |
| 2009/0151086 A1 | 6/2009 | Brun |
| 2009/0151087 A1 | 6/2009 | Mario et al. |
| 2009/0158533 A1 | 6/2009 | Hercouet |
| 2009/0162309 A1 | 6/2009 | Hercouet et al. |
| 2009/0191142 A1 | 7/2009 | Hercouet et al. |

FOREIGN PATENT DOCUMENTS

| | | |
|---|---|---|
| CA | 2 573 567 | 3/2006 |
| CH | 507 713 | 7/1971 |
| DE | 20 05 076 | 8/1970 |
| DE | 38 14 356 | 9/1988 |
| DE | 38 14 685 | 9/1988 |
| DE | 43 09 509 | 9/1994 |
| DE | 195 27 121 | 1/1997 |
| DE | 197 23 538 | 9/1998 |
| DE | 197 12 980 | 10/1998 |
| DE | 197 54 281 | 6/1999 |
| DE | 198 15 338 C1 | 9/1999 |
| DE | 100 08 640 | 8/2000 |
| DE | 199 09 661 | 9/2000 |
| DE | 199 62 869 | 6/2001 |
| DE | 100 28 723 | 12/2001 |
| DE | 100 56 266 | 5/2002 |
| DE | 101 48 571 | 4/2003 |
| DE | 101 48 671 | 4/2003 |
| DE | 20 2005 008 307 U1 | 7/2005 |
| DE | 10 2005 011 459 | 9/2006 |
| DE | 10 2005 032 798 | 1/2007 |
| DE | 10 2006 012 575 A1 | 2/2007 |
| DE | 10 2005 059 647 | 6/2007 |
| DE | 10 2006 020 050 | 10/2007 |
| DE | 10 2006 061 830 | 6/2008 |
| EP | 0 166 100 | 1/1986 |
| EP | 0 424 261 | 4/1991 |
| EP | 0 890 355 | 1/1999 |
| EP | 1 023 891 | 8/2000 |
| EP | 1 142 563 | 10/2001 |
| EP | 1 166 749 | 1/2002 |
| EP | 1 219 285 | 7/2002 |
| EP | 1 291 006 | 3/2003 |
| EP | 1 314 418 | 5/2003 |
| EP | 1 321 132 | 6/2003 |
| EP | 1 374 842 | 1/2004 |
| EP | 1 430 873 | 6/2004 |
| EP | 1 449 512 | 6/2004 |
| EP | 1 438 951 | 7/2004 |
| EP | 1 486 195 | 12/2004 |
| EP | 1 488 781 | 12/2004 |
| EP | 1 550 656 | 7/2005 |
| EP | 1 568 354 | 8/2005 |
| EP | 1 570 833 | 9/2005 |
| EP | 1 598 052 | 11/2005 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 | 3/2007 |
| EP | 1 792 602 | 6/2007 |
| EP | 1 813 254 | 8/2007 |
| EP | 1 862 198 | 12/2007 |
| EP | 1 870 085 | 12/2007 |
| EP | 1 902 703 | 3/2008 |
| EP | 1 927 377 | 6/2008 |
| EP | 1 944 009 | 7/2008 |
| EP | 2 005 939 | 12/2008 |
| EP | 2 011 474 | 1/2009 |
| EP | 2 018 848 | 1/2009 |
| EP | 2 072 034 | 6/2009 |
| EP | 2 072 035 | 6/2009 |
| EP | 2 072 036 | 6/2009 |
| FR | 1 517 715 | 3/1968 |
| FR | 2 132 214 | 11/1972 |
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 | 12/1999 |
| FR | 2 803 196 A1 | 7/2001 |
| FR | 2 842 101 | 1/2004 |
| FR | 2 870 724 | 12/2005 |
| FR | 2 874 323 | 2/2006 |
| FR | 2 892 623 | 5/2007 |
| FR | 2 910 309 | 6/2008 |
| FR | 2 911 499 | 7/2008 |
| FR | 2 912 903 | 8/2008 |
| FR | 2 912 904 | 8/2008 |
| FR | 2 912 906 | 8/2008 |
| FR | 2 915 886 | 11/2008 |
| FR | 2 919 499 | 2/2009 |
| FR | 2 925 304 | 6/2009 |
| FR | 2 925 307 | 6/2009 |
| FR | 2 925 308 | 6/2009 |
| FR | 2 925 309 | 6/2009 |
| FR | 2 925 311 | 6/2009 |
| GB | 1 288 128 | 9/1972 |
| GB | 2 003 938 | 3/1979 |
| GB | 1 554 331 | 10/1979 |
| GB | 2 065 177 | 6/1981 |
| GB | 2 142 348 | 1/1985 |
| GB | 2 170 830 | 8/1986 |
| GB | 2 188 948 | 10/1987 |
| GB | 2 217 735 | 11/1989 |
| JP | 58-035106 | 3/1983 |
| JP | 59-106413 | 6/1984 |
| JP | 1-165514 | 6/1989 |
| JP | 10-101537 | 4/1998 |
| JP | 2001-233748 | 8/2001 |
| JP | 2001-302471 | 10/2001 |
| JP | 2003-095984 | 4/2003 |
| JP | 2003-238370 | 8/2003 |
| JP | 2004-262886 | 9/2004 |
| JP | 2006-282524 | 10/2006 |
| JP | 2008-74705 | 4/2008 |
| WO | WO 91/11985 | 8/1991 |
| WO | WO 97/01323 | 1/1997 |
| WO | WO 97/04739 | 2/1997 |
| WO | WO 97/12587 | 4/1997 |
| WO | WO 98/03150 | 1/1998 |
| WO | WO 01/28508 | 4/2001 |

| WO | WO 01/41723 | 6/2001 |
| WO | WO 01/43709 | 6/2001 |
| WO | WO 01/60327 | 8/2001 |
| WO | WO 02/089748 | 11/2002 |
| WO | WO 03/053329 | 7/2003 |
| WO | WO 03/084495 | 10/2003 |
| WO | WO 2005/025525 | 3/2005 |
| WO | WO 2005/055966 | 6/2005 |
| WO | WO 2006/026851 A1 | 3/2006 |
| WO | WO 2007/006418 | 1/2007 |
| WO | WO 2007/096027 | 8/2007 |
| WO | WO 2008/021641 | 2/2008 |
| WO | WO 2008/096497 | 8/2008 |
| WO | WO 2008/138844 | 11/2008 |
| WO | WO 2009/080667 | 7/2009 |
| WO | WO 2009/080668 | 7/2009 |
| WO | WO 2009/080669 | 7/2009 |
| WO | WO 2009/080670 | 7/2009 |

OTHER PUBLICATIONS

Copending U.S. Appl. No. 12/642,468, filed Dec. 18, 2009.
Copending U.S. Appl. No. 12/642,473, filed Dec. 18, 2009.
Copending U.S. Appl. No. 12/642,489, filed Dec. 18, 2009.
Copending U.S. Appl. No. 12/642,492, filed Dec. 18, 2009.
Copending U.S. Appl. No. 12/642,506, filed Dec. 18, 2009.
Copending U.S. Appl. No. 12/642,513, filed Dec. 18, 2009.
Copending U.S. Appl. No. 12/642,531, filed Dec. 18, 2009.
Copending U.S. Appl. No. 12/642,536, filed Dec. 18, 2009.
Copending U.S. Appl. No. 12/642,543, filed Dec. 18, 2009.
Copending U.S. Appl. No. 12/642,551, filed Dec. 18, 2009.
Copending U.S. Appl. No. 12/642,555, filed Dec. 18, 2009.
Copending U.S. Appl. No. 12/642,568, filed Dec. 18, 2009.
Copending U.S. Appl. No. 12/642,575, filed Dec. 18, 2009.
Copending U.S. Appl. No. 12/642,583, filed Dec. 18, 2009.
Copending U.S. Appl. No. 12/642,592, filed Dec. 18, 2009.
Copending U.S. Appl. No. 12/642,593, filed Dec. 18, 2009.
Copending U.S. Appl. No. 12/642,599, filed Dec. 18, 2009.
Copending U.S. Appl. No. 12/642,624, filed Dec. 18, 2009.
Copending U.S. Appl. No. 12/642,637, filed Dec. 18, 2009.
Copending U.S. Appl. No. 12/809,140, filed Jun. 18, 2010.
English language Abstract of DE 10 2005 011 459, dated Sep. 14, 2006.
English language Abstract of DE 10 2005 032 798, dated Jan. 25, 2007.
English language Abstract of DE 10 2005 059 647, dated Jun. 14, 2007.
English language Abstract of DE 10 2006 012 575, dated Feb. 8, 2007.
English language Abstract of DE 10 2006 020 050, dated Oct. 31, 2007.
English language Abstract of DE 10 2006 061 830, dated Jun. 26, 2008.
English language abstract of DE 100 28 723, dated Dec. 10, 2001.
English language Abstract of DE 100 56 266, dated May 23, 2002.
English language Abstract of DE 101 48 571, dated Apr. 24, 2003.
English language Abstract of DE 101 48 671, dated Apr. 10, 2003.
English language Abstract of DE 195 27 121, dated Jan. 30, 1997.
English language Abstract of DE 197 12 980, dated Oct. 1, 1998.
English language Abstract of DE 197 23 538, dated Sep. 17, 1998.
English language Abstract of DE 199 62 869, dated Jun. 28, 2001.
English language Abstract of DE 38 14 356, dated Sep. 8, 1988.
English language Abstract of DE 43 09 509, dated Sep. 19, 1994.
English language Abstract of EP 1 166 749, dated Jan. 22, 2002.
English language Abstract of EP 1 321 132, dated Jun. 25, 2003.
English language Abstract of EP 1 568 354, dated Aug. 31, 2005.
English language Abstract of EP 1 862 198, dated Dec. 5, 2007.
English language Abstract of EP 2 005 939, dated Dec. 24, 2008.
English language Abstract of EP 2 018 848, dated Jan. 28, 2009.
English language Abstract of FR 2 616 324, dated Dec. 16, 1988.
English language Abstract of FR 2 779 949, dated Dec. 24, 1999.
English language Abstract of FR 2 842 101, dated Jan. 16, 2004.
English language Abstract of FR 2 870 724, dated Dec. 2, 2005.
English language Abstract of FR 2 910 309, dated Jun. 27, 2008.
English language Abstract of FR 2 911 499, dated Jul. 25, 2008.
English language Abstract of FR 2 912 903, dated Aug. 29, 2008.
English language Abstract of FR 2 912 904, dated Aug. 29, 2008.
English language Abstract of FR 2 912 906, dated Aug. 29, 2008.
English language Abstract of FR 2 915 886, dated Nov. 14, 2008.
English language Abstract of FR 2 919 499, dated Feb. 6, 2009.
English language Abstract of FR 2 925 304, dated Jun. 26, 2009.
English language Abstract of FR 2 925 308, dated Jun. 26, 2009.
English language Abstract of FR 2 925 309, dated Jun. 26, 2009.
English language Abstract of JP 1-165514, dated Jun. 29, 1989.
English language Abstract of JP 2001-233748, dated Aug. 28, 2001.
English language Abstract of JP 2001-302471, dated Oct. 31, 2001.
English language Abstract of JP 2003-095984, dated Apr. 3, 2003.
English language Abstract of JP 2003-238370, dated Aug. 27, 2003.
English language Abstract of JP 2004-262886, dated Sep. 24, 2004.
English language Abstract of JP 2006-282524, dated Oct. 19, 2006.
English language Abstract of JP 2008-074705, dated Apr. 3, 2008.
English language Abstract of JP 58-035106, dated Mar. 1, 1983.
English language Abstract of JP 59-106413, dated Jun. 20, 1984.
English language Abstract of WO 2007/096027, dated Aug. 30, 2007.
English language Abstract of WO 2008/096497, dated Aug. 14, 2008.
English language Abstract of WO 91/11985, dated Aug. 22, 1991.
English language Abstract of WO 97/04739, dated Feb. 13, 1997.
European Search Report for EP 08 17 2444, dated Apr. 13, 2009.
European Search Report for EP 08 17 2449, dated Apr. 13, 2009.
European Search Report for EP 08 17 2454, dated Apr. 3, 2009.
European Search Report for EP 09 17 9779, dated May 5, 2010.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9914, dated Mar. 25, 2010.
European Search Report for EP 09 17 9992, dated Mar. 24, 2010.
European Search Report for EP 09 18 0003, dated Feb. 24, 2010.
European Search Report for EP 10 15 5935, dated Oct. 8, 2010.
French Search Report for FR 07/60273, dated Aug. 20, 2008.
French Search Report for FR 07/60274, dated Aug. 20, 2008.
French Search Report for FR 07/60277, dated Aug. 20, 2008.
French Search Report for FR 07/60278, dated Aug. 20, 2008.
French Search Report for FR 08/07283, dated Sep. 30, 2009.
French Search Report for FR 08/07285, dated Sep. 28, 2009.
French Search Report for FR 08/07286, dated Sep. 24, 2009.
French Search Report for FR 08/07287, dated Oct. 13, 2009.
French Search Report for FR 08/07288, dated Nov. 4, 2009.
French Search Report for FR 08/07290, dated Oct. 14, 2009.
French Search Report for FR 08/07291, dated Oct. 19, 2009.
French Search Report for FR 08/07292, dated Aug. 25, 2009.
French Search Report for FR 08/07294, dated Aug. 19, 2009.
French Search Report for FR 08/07298, dated Nov. 2, 2009.
French Search Report for FR 08/07304, dated Oct. 1, 2009.
French Search Report for FR 08/07306, dated Aug. 13, 2009.
French Search Report for FR 08/07307, dated Aug. 24, 2009.
French Search Report for FR 08/07309, dated Aug. 3, 2009.
French Search Report for FR 08/07310, dated Oct. 2, 2009.
French Search Report for FR 08/07312, dated Oct. 1, 2009.
French Search Report for FR 08/07313, dated Aug. 26, 2009.
French Search Report for FR 08/07314, dated Aug. 27, 2009.
French Search Report for FR 08/07315, dated Nov. 11, 2009.
French Search Report for FR 08/07316, dated Nov. 18, 2009.
French Search Report for FR 08/07319, dated Aug. 3, 2009.
French Search Report for FR 08/07320, dated Sep. 15, 2009.
French Search Report for FR 08/07322, dated Sep. 24, 2009.
French Search Report for FR 08/07323, dated Sep. 24, 2009.
French Search Report for FR 08/58838, dated Sep. 3, 2009.
French Search Report for FR 08/58840, dated Sep. 30, 2009.
French Search Report for FR 08/58880, dated Sep. 18, 2009.
French Search Report for FR 08/58881, dated Sep. 29, 2009.
French Search Report for FR 08/58886, dated Nov. 3, 2009.

French Search Report for FR 08/58888, dated Nov. 3, 2009.
French Search Report for FR 08/58889, dated Sep. 30, 2009.
French Search Report for FR 08/58890, dated Sep. 21, 2009.
French Search Report for FR 08/58891, dated Aug. 24, 2009.
French Search Report for FR 08/58892, dated Sep. 24, 2009.
French Search Report for FR 09/51367, dated Jan. 29, 2010.
French Search Report for FR 09/54264, dated Mar. 5, 2010.
French Search Report for FR 09/56389, dated Jun. 14, 2010.
French Search Report for FR 09/57176, dated Jun. 17, 2010.
International Search Report for PCT/FR2009/052617, dated Mar. 30, 2010.
Notice of Allowance mailed Aug. 10, 2010, in U.S. Appl. No. 12/339,820.
Notice of Allowance mailed Aug. 26, 2010, in U.S. Appl. No. 12/642,624.
Notice of Allowance mailed Aug. 26, 2010, in U.S. Appl. No. 12/642,637.
Notice of Allowance mailed Aug. 27, 2010, in U.S. Appl. No. 12/642,513.
Notice of Allowance mailed in co-pending U.S. Appl. No. 12/339,753, dated Jul. 9, 2010.
Notice of Allowance mailed Jun. 11, 2010, in U.S. Appl. No. 12/642,489.
Notice of Allowance mailed Nov. 19, 2010, in U.S. Appl. No. 12/339,820.
Notice of Allowance mailed Nov. 26, 2010, in U.S. Appl. No. 12/642,513.
Notice of Allowance mailed Nov. 26, 2010, in U.S. Appl. No. 12/642,543.
Notice of Allowance mailed Nov. 30, 2010, in U.S. Appl. No. 12/642,624.
Notice of Allowance mailed Oct. 26, 2010, in U.S. Appl. No. 12/339,753.
Notice of Allowance mailed Sep. 16, 2010, in U.S. Appl. No. 12/642,555.
Notice of Allowance mailed Sep. 21, 2010, in U.S. Appl. No. 12/642,489.
Notice of Allowance mailed Sep. 22, 2010, in U.S. Appl. No. 12/642,551.
Notice of Allowance mailed Sep. 23, 2010, in U.S. Appl. No. 12/642,536.
Notice of Allowance mailed Sep. 7, 2010, in U.S. Appl. No. 12/642,599.
Notice of Allowance mailed Sep. 8, 2010, in U.S. Appl. No. 12/642,543.
Notice of Allowance mailed Sep. 9, 2010, in U.S. Appl. No. 12/642,531.
Office Action mailed Aug. 11, 2010, in co-pending U.S. Appl. No. 12/642,593.
Office Action mailed Aug. 26, 2010, in co-pending U.S. Appl. No. 12/642,473.
Office Action mailed Feb. 1, 2010, in co-pending U.S. Appl. No. 12/339,753.
Office Action mailed Mar. 15, 2010, in co-pending U.S. Appl. No. 12/339,820.
Office Action mailed Sep. 17, 2010, in co-pending U.S. Appl. No. 12/642,506.
Office Action mailed Sep. 21, 2010, in co-pending U.S. Appl. No. 12/642,468.
Office Action mailed Sep. 22, 2010, in co-pending U.S. Appl. No. 12/642,492.
Office Action mailed Sep. 3, 2010, in co-pending U.S. Appl. No. 12/642,451.
STIC Search Report for U.S. Appl. No. 12/339,820, dated Jan. 21, 2010.
STIC Search Report for U.S. Appl. No. 12/642,492, dated Jul. 14, 2010.

* cited by examiner

READY-TO-USE COMPOSITION FOR OXIDATION DYEING OF KERATIN FIBERS COMPRISING AT LEAST ONE FATTY SUBSTANCE, AT LEAST ONE THICKENER, AT LEAST ONE DYE PRECURSOR, AT LEAST ONE OXIDIZING AGENT, AND AT LEAST ONE ALKALINE AGENT, AND PROCESS AND KITS THEREWITH

This application claims benefit of U.S. Provisional Application No. 61/150,099, filed Feb. 5, 2009. This application also claims benefit of priority under 35 U.S.C. §119 to French Patent Application No. 0807321, filed Dec. 19, 2008.

Disclosed herein is a ready-to-use composition for the oxidation dyeing of keratin fibers.

Dyeing of keratin fibers such as human hair with dyeing compositions comprising oxidation dyes, for example, precursors of oxidation dyes and color modifiers, may be generally known.

The precursors of oxidation dyes, generally called oxidation bases, may be initially colorless or faintly colored compounds which, in combination with oxidizing products, can give rise by a process of oxidative condensation to colored and coloring compounds. These can be compounds such as ortho- or para-phenylenediamines, ortho- or para-aminophenols and heterocyclic bases.

It may be also known that the shades obtained with these oxidation bases can be varied by combining them with couplers or color modifiers, the latter generally being chosen from meta-diaminobenzenes, meta-aminophenols, meta-diphenols and certain heterocyclic compounds such as indole compounds.

The variety of the molecules employed for the oxidation bases and couplers can make it possible to obtain a rich palette of colors.

The so-called "permanent" coloration obtained using these oxidation dyes, also called oxidation coloring, should moreover satisfy at least one of a certain number of requirements. Thus, it should be harmless from the toxicological standpoint, it should permit shades to be obtained of the desired intensity and should have good resistance to external aggressive factors such as light, weather, washing, perming, sweat and/or rubbing.

The dyes should also be able to cover white hair, and finally should have minimal selectivity, i.e. should give the smallest possible differences in coloration along one and the same keratin fiber, which generally has zones that are sensitized (i.e. damaged) to a varying extent from its tip to its root.

There have been numerous attempts in the field of hair coloring to improve dyeing properties, for example via additives. However, selection of these additives can be difficult, since they should improve the dyeing properties of the dyeing compositions without adversely affecting the other properties of said compositions. For example, these additives should not have an adverse effect on the properties of lightening of keratin fibers and the properties of application of the coloration.

Accordingly, one aspect of the present disclosure are novel ready-to-use compositions for the oxidation dyeing of keratin fibers that can avoid at least one of the drawbacks of the prior art. For example, disclosed here in are ready-to-use compositions for oxidation coloring of keratin fibers, displaying improved dyeing properties that can make it possible to achieve the desired lightening and can be easy to mix and apply, for example, which do not flow and which can stay at the point of application. "Improved dyeing properties" means, for example, an improvement with respect to the strength/intensity and/or the uniformity of dyeing.

Provided herein is a ready-to-use composition for the oxidation dyeing of keratin fibers, and for example, of human keratin fibers such as the hair, comprising, A) at least one fatty substance other than fatty acids, which is present in the ready-to-use composition in an amount of greater than or equal to 25% by weight relative to the total weight of the ready-to-use composition, B) at least one polymeric thickener, C) at least one dye precursor, D) at least one oxidizing agent and E) at least one alkaline agent wherein at least one of the at least one alkaline agent is an organic amine.

The ready-to-use composition according to the present disclosure may have improved dyeing properties. For example, the ready-to-use composition of the disclosure may give coloring that has good strength and/or intensity and/or good uniformity of the color along the fiber between the tip and the root of the hair (also called the selectivity of coloring) and/or good chromaticity. The ready-to-use composition of the disclosure can be applied without difficulty on the keratin fibers, without running. This ready-to-use composition may also lead to less degradation of the keratin fibers in the course of the coloring process.

Finally, the coloring obtained via of the ready-to-use compositions of the disclosure may be durable, and resistant to the various external aggressive factors to which keratin fibers may be subjected.

Provided herein is also a method of dyeing of keratin fibers, comprising applying to the keratin fibers, for a sufficient time to develop the desired coloration, the ready-to-use composition as defined previously.

Further provided herein is a multi-compartment kit for application of the ready-to-use composition of the disclosure.

As has been mentioned, the ready-to-use composition of the disclosure comprises at least one fatty substance other than fatty acids.

"Fatty substance" means an organic compound insoluble in water at normal temperature (25° C.) and at atmospheric pressure (760 mmHg) (solubility below 5% and such as below 1% and further such as below 0.1%). Fatty substances have in their structure a chain of at least two siloxane groups or at least one hydrocarbon chain having at least 6 carbon atoms. Moreover, fatty substances are generally soluble in organic solvents in the same conditions of temperature and pressure, for example in chloroform, ethanol, benzene or decamethylcyclopentasiloxane.

According to the present disclosure, the ready-to-use composition comprises at least 25% of fatty substances by weight relative to the total weight of the ready-to-use composition, these substances being other than fatty acid.

Fatty substances are, for example, chosen from lower alkanes, fatty alcohols, esters of fatty acid, esters of fatty alcohol, oils such as mineral, vegetable, animal and synthetic non-silicone oils, non-silicone waxes and silicones.

In some embodiments, the alcohols and esters have at least one linear or branched, saturated or unsaturated hydrocarbon group, comprising 6 to 30 carbon atoms, optionally substituted, for example, with at least one hydroxyl group (for example 1 to 4). If they are unsaturated, these compounds can have one to three, conjugated or unconjugated, carbon-carbon double bonds.

With regard to the lower alkanes, in some embodiments, these have from 6 to 16 carbon atoms and are linear or branched, optionally cyclic. As examples, alkanes can be chosen from hexane and dodecane, isoparaffins such as isohexadecane and isodecane.

Non-limiting examples of non-silicone oils usable in the ready-to-use composition of the disclosure, include:

hydrocarbon oils of animal origin, such as perhydrosqualene;

hydrocarbon oils of vegetable origin, such as liquid triglycerides of fatty acids having from 6 to 30 carbon atoms such as triglycerides of heptanoic or octanoic acids, or for example sunflower oil, maize oil, soya oil, cucurbit oil, grapeseed oil, sesame oil, hazelnut oil, apricot oil, macadamia oil, arara oil, sunflower oil, castor oil, avocado oil, triglycerides of caprylic/capric acids such as those sold by the company Stearineries Dubois or those sold under the names MIGLYOL® 810, 812 and 818 by the company Dynamit Nobel, jojoba oil, shea butter oil;

hydrocarbons with more than 16 carbon atoms, linear or branched, of mineral or synthetic origin, such as paraffin oils, petroleum jelly, liquid paraffin, polydecenes, hydrogenated polyisobutene such as Parleam®.

fluorinated, partially hydrocarbon oils; as fluorinated oils, non-limiting examples include perfluoromethylcyclopentane and perfluoro-1,3-dimethylcyclohexane, sold under the names "FLUTEC® PC1" and "FLUTEC® PC3" by the company BNFL Fluorochemicals; perfluoro-1,2-dimethylcyclobutane; perfluoroalkanes such as dodecafluoropentane and tetradecafluorohexane, sold under the names "PF 5050®" and "PF 5060®" by the 3M Company, or bromoperfluorooctyl sold under the name "FORALKYL®" by the company Atochem; nonafluoro-methoxybutane and nonafluoroethoxyisobutane; derivatives of perfluoromorpholine, such as 4-trifluoromethyl perfluoromorpholine sold under the name "PF 5052®" by the 3M Company.

The fatty alcohols usable as fatty substances in the ready-to-use composition of the disclosure include, but are not limited to, non-alkoxylated, saturated or unsaturated, linear or branched, and have from 6 to 30 carbon atoms and more particularly from 8 to 30 carbon atoms; For example, cetyl alcohol, stearyl alcohol and their mixture (cetylstearyl alcohol), octyldodecanol, 2-butyloctanol, 2-hexyldecanol, 2-undecylpentadecanol, oleic alcohol or linoleic alcohol.

The exemplary non-silicone wax or waxes that can be used in the ready-to-use composition of the disclosure are chosen from carnauba wax, candelilla wax, and Alfa wax, paraffin wax, ozokerite, vegetable waxes such as olive wax, rice wax, hydrogenated jojoba wax or absolute waxes of flowers such as the essential wax of blackcurrant flower sold by the company BERTIN (France), animal waxes such as beeswaxes, or modified beeswaxes (cerabellina); other waxes or waxy raw materials usable according to the disclosure are, for example, marine waxes such as that sold by the company SOPHIM under reference M82, waxes of polyethylene or of polyolefins in general.

The exemplary fatty acid esters are the esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total number of carbons of the esters being, for example, greater than or equal to 10.

Among the monoesters, non-limiting mentions can be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, ethyl-2-hexyl palmitate, 2-octyldecyl palmitate, alkyl myristates such as isopropyl, butyl, cetyl, 2-octyldodecyl, mirystyl, stearyl myristate, hexyl stearate, butyl stearate, isobutyl stearate; dioctyl malate, hexyl laurate, and 2-hexyldecyl laurate.

Further non-limiting mentions of esters can be made of the esters of $C_4$-$C_{22}$ di- or tricarboxylic acids and of $C_1$-$C_{22}$ alcohols and the esters of mono-, di- or tricarboxylic acids and of $C_2$-$C_{26}$ di-, tri-, tetra- or pentahydroxy alcohols.

Even further non-limiting examples of esters include: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate, tridecyl erucate; triisopropyl citrate; triisotearyl citrate; glyceryl trilactate; glyceryl trioctanoate; trioctyldodecyl citrate; trioleyl citrate, propylene glycol dioctanoate; neopentyl glycol diheptanoate; diethylene glycol diisanonate; and polyethylene glycol distearates.

Among the esters mentioned above, exemplary esters include ethyl, isopropyl, myristyl, cetyl, stearyl palmitates, ethyl-2-hexyl palmitate, 2-octyldecyl palmitate, alkyl myristates such as isopropyl, butyl, cetyl, 2-octyldodecyl myristate, hexyl stearate, butyl stearate, isobutyl stearate; dioctyl malate, hexyl laurate, 2-hexyldecyl laurate and isononyl isononanate, cetyl octanoate.

The ready-to-use composition can also comprise, as fatty ester, esters and di-esters of sugars of $C_6$-$C_{30}$, such as $C_{12}$-$C_{22}$ fatty acids. "Sugar" as used in the disclosure means oxygen-containing hydrocarbon compounds that possess several alcohol functions, with or without aldehyde or ketone functions, and having at least 4 carbon atoms. These sugars can be monosaccharides, oligosaccharides or polysaccharides.

As suitable sugars, non-limiting examples include sucrose, glucose, galactose, ribose, fucose, maltose, fructose, mannose, arabinose, xylose, lactose, and their derivatives, for example alkylated, such as methylated derivatives such as methylglucose.

The esters of sugars and of fatty acids can, for example, be chosen from the esters or mixtures of esters of sugars described previously and of linear or branched, saturated or unsaturated $C_6$-$C_{30}$, such as $C_{12}$-$C_{22}$ fatty acids. If they are unsaturated, these compounds can have one to three, conjugated or unconjugated, carbon-carbon double bonds.

The esters according to at least one embodiment can also be chosen from mono-, di-, tri- and tetra-esters, polyesters and mixtures thereof.

These esters can be for example oleate, laurate, palmitate, myristate, behenate, cocoate, stearate, linoleate, linolenate, caprate, arachidonates, or mixtures thereof such as the oleo-palmitate, oleo-stearate, palmito-stearate mixed esters.

For example, the mono- and di-esters can be used, and such as the mono- or di-oleate, stearate, behenate, oleopalmitate, linoleate, linolenate, oleostearate, of sucrose, of glucose or of methylglucose.

Non-limiting mention can be made of the product sold under the name GLUCATE® DO by the company Amerchol, which is a dioleate of methylglucose.

Exemplary esters or of mixtures of esters of sugar of fatty acid include:
- the products sold under the names F160, F140, F110, F90, F70, SL40 by the company Crodesta, denoting respectively the palmito-stearates of sucrose formed from 73% of monoester and 27% of di- and tri-ester, from 61% of monoester and 39% of di-, tri-, and tetra-ester, from 52% of monoester and 48% of di-, tri-, and tetra-ester, from 45% of monoester and 55% of di-, tri-, and tetra-ester, from 39% of monoester and 61% of di-, tri-, and tetra-ester, and the mono-laurate of sucrose;
- the products sold under the name Ryoto Sugar Esters for example with the reference B370 and corresponding to the behenate of sucrose formed from 20% of monoester and 80% of di-triester-polyester;
- sucrose mono-di-palmito-stearate marketed by the company Goldschmidt under the name TEGOSOFT® PSE.

The silicones usable in the ready-to-use composition of the present disclosure include but are not limited to volatile or non-volatile, cyclic, linear or branched silicones, modified or not with organic groups, having a viscosity from 5.10-6 to 2.5 m2/s at 25° C. such as from 1.10-5 to 1 m2/s.

The silicones usable according to the disclosure can be in the form of oils, waxes, resins or gums.

In some embodiments, the silicone is chosen from the polydialkylsiloxanes, such as the polydimethylsiloxanes (PDMS), and the organo-modified polysiloxanes having at least one functional group selected from the poly(alkoxylated) groups, the amine groups and the alkoxy groups.

The organopolysiloxanes are defined in more detail in the work of Walter NOLL "Chemistry and Technology of Silicones" (1968), Academic Press. They can be volatile or non-volatile.

When they are volatile, the silicones are, for example, chosen from those with a boiling point between 60° C. and 260° C., and for further examples, chosen from:
- the cyclic polydialkylsiloxanes having from 3 to 7, such as from 4 to 5 silicon atoms. It can be, for example, the octamethylcyclotetrasiloxane marketed under the name VOLATILE SILICONE® 7207 by UNION CARBIDE or SILBIONE® 70045 V2 by RHODIA, the decamethylcyclopentasiloxane marketed under the name VOLATILE SILICONE® 7158 by UNION CARBIDE, and SILBIONE® 70045 V5 by RHODIA, and mixtures thereof.

Non-limiting mentions can also be made of the cyclocopolymers of the dimethylsiloxanes/methylalkylsiloxane type, such as SILICONE VOLATILE® FZ 3109 marketed by the company UNION CARBIDE, of the formula:

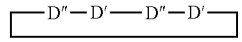

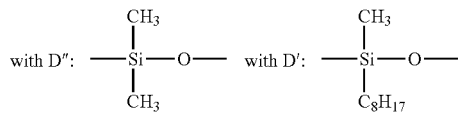

Non-limiting mentions can further be made of the mixtures of cyclic polydialkylsiloxanes with organic compounds derived from silicon, such as the mixture of octamethylcyclotetrasiloxane and tetratrimethylsilylpentaerythritol (50/50) and the mixture of octamethylcyclotetrasiloxane and oxy-1,1'-(hexa-2,2,2',2',3,3'-trimethylsilyloxy) bis-neopentane.

Other suitable volatile silicones include the linear volatile polydialkylsiloxanes having 2 to 9 silicon atoms and with a viscosity less than or equal to $5.10^{-6}$ m$^2$/s at 25° C. An example is decamethyltetrasiloxane, marketed under the name "SH 200" by the company TORAY SILICONE. Silicones included in this class are also described in the article published in Cosmetics and Toiletries, Vol. 91, Jan. 76, p. 27-32—TODD BYERS "Volatile Silicone fluids for cosmetics".

Even further non-limiting mentions can be made of non-volatile polydialkylsiloxanes, gums and resins of polydialkylsiloxanes, polyorganosiloxanes modified with the aforementioned organofunctional groups, and mixtures thereof.

These silicones are, for example, chosen from the polydialkylsiloxanes, such as the polydimethylsiloxanes with trimethylsilyl end groups. The viscosity of the silicones is measured at 25° C. according to standard ASTM 445 Appendix C.

Among these polydialkylsiloxanes, mention can be made of, non-exhaustively, the following commercial products:
- the SILBIONE® oils of series 47 and 70 047 or the MIRASIL® oils marketed by RHODIA, for example the oil 70 047 V 500 000;
- the oils of the MIRASIL® series marketed by the company RHODIA;
- the oils of the 200 series from the company DOW CORNING such as DC200, with a viscosity of 60 000 mm$^2$/s;
- the VISCASIL® oils from GENERAL ELECTRIC and certain oils of the SF series (SF 96, SF 18) from GENERAL ELECTRIC.

Non-limiting mention can also be made of the polydimethylsiloxanes with dimethylsilanol end groups known under the name of dimethiconol (CTFA), such as the oils of the 48 series from the company RHODIA.

In this class of polydialkylsiloxanes, non-limiting mentions can be made of the products marketed under the names "ABIL WAX® 9800 and 9801" by the company GOLDSCHMIDT, which are polydialkyl ($C_1$-$C_{20}$) siloxanes.

The silicone gums usable according to the disclosure are, for example, polydialkylsiloxanes, such as polydimethylsiloxanes with high number-average molecular weights between 200,000 and 1,000,000 used alone or mixed in a solvent. This solvent can be chosen from the volatile silicones, the polydimethylsiloxane (PDMS) oils, the polyphenylmethylsiloxane (PPMS) oils, the isoparaffins, the polyisobutylenes, methylene chloride, pentane, dodecane, tridecane and mixtures thereof.

Products usable according to the disclosure are, for example, mixtures such as:
- mixtures formed from a chain end hydroxylated polydimethylsiloxane, or dimethiconol (CTFA) and a cyclic polydimethylsiloxane also called cyclomethicone (CTFA), such as the product Q2 1401 marketed by the company DOW CORNING;
- mixtures of a polydimethylsiloxane gum and a cyclic silicone such as the product SF 1214 Silicone Fluid from the company GENERAL ELECTRIC, said product being a gum SF 30 corresponding to a dimethicone, having a number-average molecular weight of 500,000, dissolved in the oil SF 1202 Silicone Fluid corresponding to decamethylcyclopentasiloxane;
- mixtures of two PDMS of different viscosities, for example, of a PDMS gum and a PDMS oil, such as the product SF 1236 from the company GENERAL ELECTRIC. The product SF 1236 is a mixture of a gum SE 30 as defined above having a viscosity of 20 m$^2$/s and an oil SF 96 with a viscosity of $5.10^{-6}$ m$^2$/s. This product, for example, has 15% of gum SE 30 and 85% of oil SF 96.

The organopolysiloxane resins usable according to the disclosure include but are not limited to crosslinked siloxane systems containing the units:

$R_2SiO_{2/2}$, $R_3SiO_{1/2}$, $RSiO_{3/2}$ and $SiO_{4/2}$ in which R represents an alkyl having 1 to 16 carbon atoms. For example, R denotes a $C_1$-$C_4$ lower alkyl group such as methyl.

Among these resins, non-limiting mention can be made of the product marketed under the name "DOW CORNING 593" or those marketed under the names "SILICONE FLUID SS 4230 and SS 4267" by the company GENERAL ELECTRIC, which are silicones of dimethyl/trimethyl siloxane structure.

Non-limiting mention can also be made of the resins of the trimethylsiloxysilicate type, such as those marketed under the names X22-4914, X21-5034 and X21-5037 by the company SHIN-ETSU.

The organomodified silicones usable according to the disclosure include but are not limited to silicones as defined previously, having in their structure at least one organofunctional group fixed by a hydrocarbon group.

In addition to the silicones described above, the organomodified silicones can be polydiaryl siloxanes, such as polydiphenylsiloxanes, and polyalkyl-arylsiloxanes functionalized by the aforementioned organofunctional groups.

The polyalkarylsiloxanes are, for example, chosen from the polydimethyl/methylphenylsiloxanes, the polydimethyl/diphenylsiloxanes, linear and/or branched, with viscosity ranging from 1.10-5 to $5.102 \text{ m}^2/\text{s}$ at 25° C.

Among these polyalkarylsiloxanes, non-limiting mentins can be made of the products marketed under the following names:

the SILBIONE® oils of series 70 641 from RHODIA;
the oils of the series RHODORSIL® 70 633 and 763 from RHODIA;
the oil DOW CORNING 556 COSMETIC GRADE FLUID from DOW CORNING;
the silicones of the PK series from BAYER such as the product PK20;
the silicones of the series PN, PH from BAYER such as the products PN1000 and PH1000;
certain oils of the SF series from GENERAL ELECTRIC such as SF 1023, SF 1154, SF 1250, SF 1265.

Among the organomodified silicones, non-limiting mention can be made of the polyorganosiloxanes having:

polyoxyethylene and/or polyoxypropylene groups optionally with $C_6$-$C_{24}$ alkyl groups such as the products called dimethicone copolyol marketed by the company DOW CORNING under the name DC 1248 or the oils SILWET® L 722, L 7500, L 77, L 711 from the company UNION CARBIDE and the alkyl ($C_{12}$)-methicone copolyol marketed by the company DOW CORNING under the name Q2 5200;
substituted or unsubstituted amine groups such as the products marketed under the name GP 4 Silicone Fluid and GP 7100 by the company GENESEE or the products marketed under the names Q2 8220 and DOW CORNING 929 or 939 by the company DOW CORNING. The substituted amine groups are, for example, $C_1$-$C_4$ aminoalkyl groups;
alkoxylated groups, such as the product marketed under the name "SILICONE COPOLYMER F-755" by SWS SILICONES and ABIL WAX® 2428, 2434 and 2440 by the company GOLDSCHMIDT.

In some embodiments, the at least one fatty substance is neither alkoxylated, nor glycerolated.

For example, the at least one fatty substance is chosen from compounds that are liquid or pasty at room temperature and at atmospheric pressure.

For further example, the at least one fatty substance is a compound that is liquid at a temperature of 25° C. and at atmospheric pressure.

The at least one fatty substance is, for example, chosen from the lower alkanes, fatty alcohols, esters of fatty acid, esters of fatty alcohol, and oils such as non-silicone mineral, vegetable and synthetic oils, the silicones.

According to at least one embodiment, the at least one fatty substance is chosen from liquid paraffin, polydecenes, liquid esters of fatty acids and of fatty alcohols, and mixtures thereof, for example, the at least one fatty substance of the ready-to-use composition according to the disclosure can be non-silicone.

In some embodiments, the at least one fatty substance is chosen from alkanes, hydrocarbons and silicones.

The ready-to-use composition according to the disclosure comprises at least one fatty substance other than fatty acids, which is present in the ready-to-use composition in an amount of greater than or equal to 25% by weight relative to the total weight of the ready-to-use composition. For example, the concentration of fatty substances is from 25 to 80%, such as from 25 to 65%, further such as from 30 to 55% relative to the total weight of the ready-to-use composition.

The ready-to-use composition comprises at least one polymeric thickener.

As used herein, polymeric thickener means a polymer which, when added at 1 wt. % to an aqueous or aqueous-alcoholic solution at 30% of ethanol, and at pH=7 or to an oil chosen from liquid paraffin, isopropyl myristate and cyclopentadimethylsiloxane, gives a viscosity of at least 100 cP, such as at least 500 cP, at 25° C. and at a shear rate of 1s-1. This viscosity can be measured using a cone-and-plate viscosimeter (Rheometer Haake R600 or similar).

The at least one polymeric thickener can cause thickening of the aqueous phase and/or of the oil phase.

The at least one polymeric thickener can be ionic or non-ionic, associative or non-associative polymer.

As used herein, the non-associative polymeric thickeners are polymeric thickeners not containing a $C_{10}$-$C_{30}$ fatty chain.

Thickeners of the aqueous phase:

As aqueous-phase polymeric thickeners, non-limiting mention can be made of the polymeric thickeners with sugar units.

"Sugar unit" means, as used herein, a unit derived from a carbohydrate of formula Cn(H2O)n-1 or (CH2O)n, which can optionally be modified by substitution, and/or by oxidation and/or by dehydration.

The sugar units of the polymeric thickeners of the disclosure are, for example, derived from the following sugars: glucose, galactose, arabinose, rhamnose, mannose, xylose, fucose, anhydrogalactose, galacturonic acid, glucuronic acid, mannuronic acid, galactose sulphate, and/or anhydrogalactose sulphate.

Exemplary polymeric thickeners of the disclosure include:
native gums such as:
a) exudates from trees or shrubs including but not being limited to:
gum arabic (branched polymer of galactose, arabinose, rhamnose and glucuronic acid)
ghatti gum (polymer derived from arabinose, galactose, mannose, xylose and glucuronic acid)
karaya gum (polymer derived from galacturonic acid, galactose, rhamnose and glucuronic acid)

gum tragacanth (polymer of galacturonic acid, galactose, fucose, xylose and arabinose)
b) gums derived from algae, including without being limited to:
agar (polymer derived from galactose and anhydrogalactose)
alginates (polymers of mannuronic acid and glucuronic acid)
carrageenans and furcelleranes (polymers of galactose sulphate and anhydrogalactose sulphate)
c) gums derived from seeds or tubers, including without being limited to:
guar gum (polymer of mannose and galactose)
carob gum (polymer of mannose and galactose)
fenugreek gum (polymer of mannose and galactose)
tamarind gum (polymer of galactose, xylose and glucose)
konjac gum (polymer of glucose and mannose)
d) microbial gums, including without being limited to:
xanthan gum (polymer of glucose, mannose acetate, mannose/pyruvic acid and glucuronic acid)
gellan gum (polymer of partially acylated glucose, rhamnose and glucuronic acid)
scleroglucan gum (polymer of glucose)
e) plant extracts, including without being limited:
cellulose (polymer of glucose)
starch (polymer of glucose)

These polymers can be modified physically or chemically. As a physical treatment, non-limiting mention can be made of temperature treatment.

As chemical treatments, non-limiting mentions can be made of the reactions of esterification, etherification, amidation, oxidation. These treatments can give polymers which can, for example, be non-ionic, anionic or amphoteric.

For example, these chemical or physical treatments are applied to guar gums, carob gums, starches and celluloses.

The non-ionic guar gums usable according to the disclosure can be modified by $C_1$-$C_6$ hydroxyalkyl groups.

Among the hydroxyalkyl groups, non-limiting mentions can be made of the hydroxymethyl, hydroxyethyl, hydroxypropyl and hydroxybutyl groups.

These guar gums may be well known from the art and can for example be prepared by reacting the oxides of corresponding alkenes, for example propylene oxides, with guar gum to obtain a guar gum modified by hydroxypropyl groups.

The rate of hydroxyalkylation, for example, can vary from 0.4 to 1.2 and correspond to the number of molecules of alkylene oxide consumed by the number of free hydroxyl functions present on the guar gum.

The non-ionic guar gums optionally modified by hydroxyalkyl groups are for example sold under the trade names JAGUAR HP8, JAGUAR HP60 and JAGUAR HP120 by the company RHODIA CHIMIE.

The starch molecules used in the present disclosure can have, as botanical origin, cereals or tubers. Thus, the starches are chosen for example from maize starch, rice starch, manioc starch, barley starch, potato starch, wheat starch, sorghum starch, and pea starch.

The starches can be modified chemically or physically: for example, by at least one of the reactions chosen from pregelatinization, oxidation, crosslinking, esterification, etherification, amidation, and thermal treatments.

For example, these reactions can be carried out as follows:
pregelatinization, by causing the starch grains to burst (for example drying and cooking in a drying drum);
oxidation by strong oxidizing agents leading to the introduction of carboxyl groups in the starch molecule and to depolymerization of the starch molecule (for example by treating an aqueous solution of starch with sodium hypochlorite);
crosslinking by functional agents that are able to react with the hydroxyl groups of the starch molecules, which will thus be joined together (for example with glyceryl and/or phosphate groups);
esterification in alkaline medium for the grafting of functional groups, such as $C_1$-$C_6$ acyl (acetyl), $C_1$-$C_6$ hydroxyalkyls (hydroxyethyl, hydroxypropyl), carboxymethyl, or octenylsuccinic.

For example, by crosslinking with phosphorus-containing compounds, monostarch phosphates (of the type St-O—PO—(OX)2), distarch phosphates (of the type St-O—PO—(OX)—O-St) or even tristarch phosphates (of the type St-O—PO—(O-St)2) or mixtures thereof (St signifying starch) can be obtained.

X, for example, denotes the alkali metals (for example sodium or potassium), the alkaline-earth metals (for example calcium, magnesium), the salts of ammonia, the salts of amines such as those of monoethanolamine, diethanolamine, triethanolamine, amino-3-propanediol-1,2, the ammonium salts derived from the basic amino acids such as lysine, arginine, sarcosine, ornithine, or citrulline.

The phosphorus-containing compounds can be, for example, sodium tripolyphosphate, sodium orthophosphate, phosphorus oxychloride or sodium trimetaphosphate.

In some embodiments, distarch phosphates or compounds rich in distarch phosphate can be used, such as the product offered under the reference names PREJEL VA-70-T AGGL (phosphate of gelatinized, hydroxypropylated manioc distarch) or PREJEL TK1 (phosphate of gelatinized manioc distarch) or PREJEL 200 (phosphate of gelatinized acetylated manioc distarch) by the company AVEBE or STRUCTURE ZEA from NATIONAL STARCH (phosphate of gelatinized maize distarch).

In some embodiments, the starch is a starch that has undergone at least one chemical modification, such as at least one esterification.

According to the disclosure, it is also possible to use amphoteric starches, comprising at least one anionic group and at least one cationic group. The at least one anionic and at least one cationic group can be bound to the same reactive site of the starch molecule or to different reactive sites; for example, they can be bound to the same reactive site. The at least one anionic group can be of the carboxyl, phosphate or sulphate type, and such as carboxyl. The at least one cationic group can be of the primary, secondary, tertiary or quaternary amine type.

The amphoteric starches are, for example, chosen from the compounds of the following formulae:

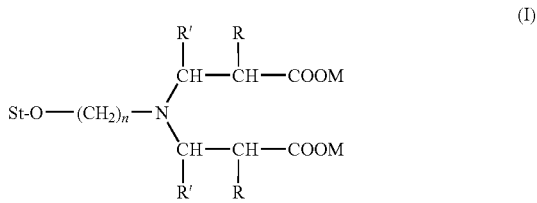

(I)

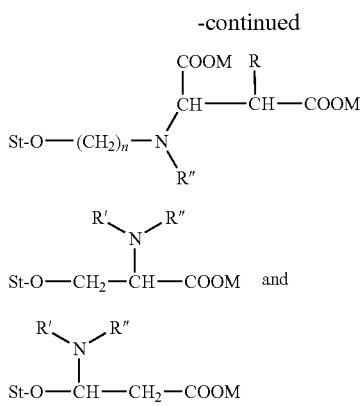

wherein

St-O represents a starch molecule,

R, which can be identical or different, represents a hydrogen atom or a methyl radical, R', which can be identical or different, represents a hydrogen atom, a methyl radical or a —COOH group, n is an integer equal to 2 or 3, M, identical or different, denotes a hydrogen atom, an alkali or alkaline-earth metal such as Na, K, L$_1$, NH$_4$, a quaternary ammonium or an organic amine, R" represents a hydrogen atom or an alkyl radical having from 1 to 18 carbon atoms.

These compounds are, for example, described in U.S. Pat. Nos. 5,455,340 and 4,017,460, which are incorporated herein by reference.

The starch molecules can be obtained from all vegetable sources of starch, such as maize, potato, oats, rice, tapioca, sorghum, barley or wheat. The hydrolysates of the aforementioned starches can also be used. The starch is, for example, obtained from potato.

In some embodiments, the starches of formulae (II) or (III) can be used. For example, the starches modified by 2-chloroethyl aminodipropionic acid can be used, i.e. the starches of formula (II) or (III) in which R, R', R" and M represent a hydrogen atom and n is equal to 2. One exemplary amphoteric starch is a starch chloroethylamidodipropionate.

As stated previously, the derivatives of celluloses can for example be anionic, amphoteric or non-ionic.

Among these derivatives, non-limiting mentions can be made of the ethers of celluloses, the esters of celluloses and the ester-ethers of celluloses.

The esters of celluloses include but are not limited to the inorganic esters of cellulose (cellulose nitrates, sulphates or phosphates etc.), the organic esters of cellulose (cellulose monoacetates, triacetates, am idopropionates, acetatebutyrates, acetatepropionates or acetatetrimellitates etc.) and the organic/inorganic mixed esters of cellulose such as cellulose acetatebutyratesulphates and cellulose acetatepropionatesuiphates. Among the ester-ethers of cellulose, non-limiting mentions can be made of the hydroxypropylmethylcellulose phthalates and the ethylcellulose sulphates.

Among the non-ionic cellulose ethers, non-limiting mention can be made of the alkylcelluloses such as the methylcelluloses and the ethylcelluloses (for example Ethocel standard 100 Premium from DOW CHEMICAL); the hydroxyalkylcelluloses such as the hydroxymethylcelluloses and the hydroxyethylcelluloses (for example Natrosol 250 HHR offered by AQUALON) and the hydroxypropylcelluloses (for example Klucel EF from AQUALON); the mixed hydroxyalkyl-alkylcelluloses such as the hydroxypropyl-methylcelluloses (for example Methocel E4M from DOW CHEMICAL), the hydroxyethyl-methylcelluloses, the hydroxyethyl-ethylcelluloses (for example Bermocoll E 481 FQ from AKZO NOBEL) and the hydroxybutyl-methylcelluloses.

Among the anionic cellulose ethers, non-limiting mention can be made of the carboxyalkylcelluloses and their salts. As examples, mention can be made of the carboxymethylcelluloses, the carboxymethylmethylcelluloses (for example Blanose 7M from the company AQUALON) and the carboxymethylhydroxyethylcelluloses and their sodium salts.

Among the non-associative polymeric thickeners without sugar units that can be used, non-limiting mention can be made of the crosslinked homopolymers or copolymers of acrylic or methacrylic acid, crosslinked homopolymers of 2-acrylamido-2-methyl-propane sulphonic acid and their crosslinked acrylamide copolymers, the homopolymers of ammonium acrylate or the copolymers of ammonium acrylate and acrylamide, alone or mixed.

Exemplary non-associative polymeric thickeners are the crosslinked homopolymers of acrylic acid.

Among the homopolymers of this type, non-limiting mention can be made of those crosslinked by an allyl alcohol ether of the sugar series, for example the products sold under the names CARBOPOLS 980, 981, 954, 2984 and 5984 by the company NOVEON or the products sold under the names SYNTHALEN M and SYNTHALEN K by the company 3 VSA.

The non-associative polymeric thickeners can also be crosslinked copolymers of (meth)acrylic acid such as the polymer sold under the name AQUA SF1 by the company NOVEON.

The non-associative polymeric thickeners can be chosen from the crosslinked homopolymers of 2-acrylamido-2-methylpropane sulphonic acid and their crosslinked acrylamide copolymers.

With regard to these homopolymers and copolymers, which can be partially or fully neutralized, non-limiting mention can be made of the polymers comprising from 90 to 99.9 wt. %, relative to the total weight of the polymer, of units of the following formula (j):

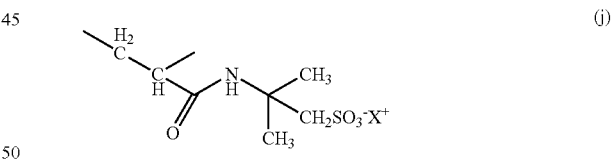

wherein X$^+$ denotes a cation or a mixture of cations, or a proton.

In some embodiments, the cations can be chosen from the alkali metals (such as sodium, potassium), the ammonium ions, unsubstituted or substituted with one to three alkyl radicals, which may be identical or different, comprising 1 to 6 carbon atoms, optionally bearing at least one hydroxyl radical, the cations derived from N-methyl-glucamine, and basic amino acids such as arginine and lysine. For example, the cation is an ammonium or sodium ion.

Moreover, the polymer may comprise from 0.01 to 10 wt %, relative to the total weight of the polymer, of crosslinking units obtained from at least one monomer having at least two ethylenic unsaturations (carbon-carbon double bond).

The crosslinking monomers having at least two ethylenic unsaturations can be chosen for example from diallyl ether, triallylcyanurate, diallylmaleate, allyl (meth)acrylate, dipropylene glycol-diallyl ether, polyglycol-diallyl ethers, triethylene glycol-divinyl ether, hydroquinone-diallyl-ether, tetraallyl-oxethanoyl, tetra- or di-ethylene glycol di(meth)acrylate, triallylamine, tetraallylethylenediamine, trimethylolpropane-diallyl ether, trimethylolpropane triacrylate, methylene-bis(meth)acrylamide or divinylbenzene, allyl alcohol ethers of the sugar series, or other allyl or vinyl ethers of polyfunctional alcohols, esters of derivatives of phosphoric and/or vinylphosphonic acid, and mixtures of said compounds.

For further details about these polymers, reference may be made to European Patent No. 815828.

Among the crosslinked copolymers of 2-acrylamido-2-methyl-propane sulphonic acid and acrylamide, partially or fully neutralized, non-limiting mention can be made of the product described in Example 1 of European Patent No. 503 853 and reference may be made to this document regarding these polymers.

The ready-to-use composition can also comprise, as non-associative polymeric thickeners, the homopolymers of ammonium acrylate or the copolymers of ammonium acrylate and acrylamide.

As examples of ammonium acrylate homopolymers, non-limning mention can be made of the product sold under the name MICROSAP PAS 5193 by the company HOECHST. Among the copolymers of ammonium acrylate and acrylamide, non-limiting mention can be made of the product sold under the name BOZEPOL C NOUVEAU or the product PAS 5193, both sold by the company HOECHST. References can be made to French Patent No. 2 416 723, and U.S. Pat. Nos. 2,798,053 and 2,923,692 regarding the description and the preparation of said compounds.

Among the thickeners, non-limiting mention can be made of the thickening systems based on associative polymers that are well known by a person skilled in the art and for example of non-ionic, anionic, cationic or amphoteric character.

It is known that the associative polymers are polymers that are able, in an aqueous medium, to form reversible associations with one another or with other molecules.

Their chemical structure comprises, for example, at least one hydrophilic zone and at least one hydrophobic zone.

As used herein, "hydrophobic group" means a radical or polymer with a hydrocarbon chain, saturated or unsaturated, linear or branched, comprising at least 10 carbon atoms, such as from 10 to 30 carbon atoms, further such as from 12 to 30 carbon atoms and even further such as from 18 to 30 carbon atoms, and further optionally comprising at least one heteroatom such as P, O, N, S, or a radical with perfluotinated or siliconized chain.

For example, the hydrocarbon group is from a monofunctional compound. For example, the hydrophobic group can be derived from a fatty alcohol such as stearyl alcohol, dodecyl alcohol, decyl alcohol. It can also denote a hydrocarbon polymer, for example polybutadiene.

Among the associative polymers of anionic type, non-limiting mention can be made of:

(I) those having at least one hydrophilic unit, and at least one fatty-chain allyl ether unit, such as those whose hydrophilic unit is constituted of an ethylenically unsaturated anionic monomer, further such as a vinylic carboxylic acid and for instance, an acrylic acid or a methacrylic acid or mixtures thereof, and whose fatty-chain allyl ether unit corresponds to the monomer of the following formula (V):

$$CH_2=CR'CH_2OB_nR \quad (V)$$

wherein R' denotes H or $CH_3$, B denotes the oxyethylene radical, n is zero or denotes an integer ranging from 1 to 100, R denotes a hydrocarbon radical chosen from alkyl, aralkyl, aryl, alkaryl, cycloalkyl radicals, comprising from 8 to 30 carbon atoms, such as from 10 to 24, and further such as from 12 to 18 carbon atoms. In some embodiments, a unit of formula (V) can be a unit in which R' denotes H, n is equal to 10, and R denotes a stearyl ($C_{18}$) radical.

Anionic associative polymers of this type can be described and prepared, according to a method of emulsion polymerization, in European Patent No. 0 216 479.

Among these anionic associative polymers, non-limiting mentions can be made of: the polymers formed from 20 to 60 wt. % of acrylic acid and/or of methacrylic acid, from 5 to 60 wt. % of (meth)acrylates of lower alkyls, from 2 to 50 wt. % of fatty-chain allyl ether of formula (V), and from 0 to 1 wt. % of a crosslinking agent, which is a well-known copolymerizable unsaturated polyethylene monomer, such as diallyl phthalate, allyl (meth)acrylate, divinylbenzene, (poly)ethylene glycol dimethacrylate, and methylene-bis-acrylamide.

Among the latter, non-limiting examples include the crosslinked terpolymers of methacrylic acid, of ethyl acrylate, of polyethylene glycol (10 EO) ether of stearyl alcohol (Steareth 10), such as those sold by the company CIBA under the names SALCARE SC80® and SALCARE SC90®, which are aqueous emulsions at 30% of a crosslinked terpolymer of methacrylic acid, of ethyl acrylate and of steareth-10-allyl ether (40/50/10).

(II) those having at least one hydrophilic unit of the unsaturated olefinic carboxylic acid type, and at least one hydrophobic unit of unsaturated alkyl ($C_{10}$-$C_{30}$) ester of carboxylic acid type.

For example, these polymers can be chosen from those whose hydrophilic unit of unsaturated olefinic carboxylic acid type corresponds to the monomer of the following formula (VI):

wherein $R_1$ denotes H or $CH_3$ or $C_2H_5$, i.e. acrylic acid, methacrylic acid or ethacrylic acid units, and whose hydrophobic unit of alkyl ($C_{10}$-$C_{30}$) ester of unsaturated carboxylic acid type corresponds to the monomer of the following formula (VII):

wherein $R_2$ denotes H or $CH_3$ or $C_2H_5$ (i.e. acrylate, methacrylate or ethacrylate units) and can be for example H (acrylate units) or $CH_3$ (methacrylate units), $R_3$ denoting a $C_{10}$-$C_{30}$, and such as $C_{12}$-$C_{22}$, alkyl radical.

Esters of ($C_{10}$-$C_{30}$) alkyls of unsaturated carboxylic acids according to the disclosure comprise, for example, lauryl acrylate, stearyl acrylate, decyl acrylate, isodecyl acrylate, dodecyl acrylate, and the corresponding methacrylates, lauryl methacrylate, stearyl methacrylate, decyl methacrylate, isodecyl methacrylate, and dodecyl methacrylate.

Anionic polymers of this type can be for example described and prepared according to U.S. Pat. Nos. 3,915,921 and 4,509,949.

Among anionic associative polymers of this type, non-limiting mentions can be made of those that are formed from a mixture of monomers comprising:

(i) essentially acrylic acid, (ii) an ester of formula (VII) described above and in which $R_2$ denotes H or $CH_3$, $R_3$ denoting an alkyl radical having from 12 to 22 carbon atoms, and (iii) a crosslinking agent, which can be a well-known copolymerizable polyethylenic unsaturated monomer, such as diallyl phthalate, allyl (meth)acrylate, divinylbenzene, (poly) ethylene glycol dimethacrylate, and methylene-bis-acrylamide.

Among anionic associative polymers of this type, non-limiting mentions can be made of those that comprise 95 to 60 wt. % of acrylic acid (hydrophilic unit), 4 to 40 wt. % of C10-C30 alkyl acrylate (hydrophobic unit), and 0 to 6 wt. % of polymerizable crosslinking monomer, or alternatively those that comprise 98 to 96 wt % of acrylic acid (hydrophilic unit), 1 to 4 wt. % of C10-C30 alkyl acrylate (hydrophobic unit), and 0.1 to 0.6 wt. % of polymerizable crosslinking monomer such as those described previously.

Among the aforementioned polymers, exemplary polymers include the products sold by the company GOODRICH under the trade names PEMULEN TR1®, PEMULEN TR2®, CARBOPOL 1382®, and even more preferably PEMULEN TR1®, and the product sold by the company S.E.P.P.I.C. under the name COATEX SX®.

Non-limiting mentions can be made of the polymers which, in addition to the monomers of formula (VI) and of formula (VII), contain at least one other monomer. The additional monomer can for example be a vinyllactam and such as vinylpyrrolidone.

As an example of polymer, mention can be made of the acrylic acid/lauryl methacrylate/vinylpyrrolidone terpolymer marketed under the name Acrylidone LM by the company ISP.

(III) the maleic anhydride/$C_{30}$-$C_{38}$ α-olefin/alkyl maleate terpolymers such as the product (maleic anhydride/$C_{30}$-$C_{38}$ α-olefin/isopropyl maleate copolymer) sold under the name PERFORMA V 1608® by the company NEW-PHASE TECHNOLOGIES.

(IV) the acrylic terpolymers comprising:

(a) 20 to 70 wt. % of a carboxylic acid with an α,β-monoethylenic unsaturation, (b) 20 to 80 wt. % of a non-surfactant monomer with an α,β-monoethylenic unsaturation different from (a), and (c) 0.5 to 60 wt. % of a non-ionic mono-urethane, which is the product of reaction of a monohydric surfactant with a monoisocyanate with a monoethylenic unsaturation, such as those described in European Patent Application No. A-0 173 109 and for example that described in Example 3, namely, a methacrylic acid/methyl acrylate/dimethyl metaisopropenyl benzyl isocyanate of ethoxylated behenyl alcohol (40EO) terpolymer in aqueous dispersion at 25%.

(V) the copolymers having, among their monomers, a carboxylic acid with an α,β-monoethylenic unsaturation and an ester of carboxylic acid with an α,β-monoethylenic unsaturation and of an alkoxylated fatty alcohol.

These compounds can also comprise, as monomer, an ester of carboxylic acid with an α,β-monoethylenic unsaturation and of C1-C4 alcohol.

As an example of this type of compound, mention can be made of ACULYN 22® sold by the company ROHM and HAAS, which is a methacrylic acid/ethyl acrylate/alkoxylated stearyl methacrylate terpolymer.

(VI) the amphiphilic polymers having at least one monomer with an ethylenic unsaturation with a sulphonic group, in free form or partially or fully neutralized and comprising at least one hydrophobic moiety. These polymers can be crosslinked or non-crosslinked. They are, for example, crosslinked.

The monomers with an ethylenic unsaturation with a sulphonic group are, for example, chosen from vinylsuiphonic acid, styrenesulphonic acid, (meth)acrylamido(C1-C22) alkylsulphonic acids, N—(C1-C22)alkyl(meth)acrylamido (C1-C22)alkylsulphonic acids such as undecyl-acrylamido-methane-sulphonic acid and partially or fully neutralized forms thereof.

For example, the (meth)acrylamido(C1-C22) alkylsulphonic acids can be used, such as acrylamido-methane-sulphonic acid, acrylamido-ethane-sulphonic acid, acrylamido-propane-sulphonic acid, 2-acrylamido-2-methylpropane-sulphonic acid, methacrylamido-2-methylpropane-sulphonic acid, 2-acrylamido-n-butane-sulphonic acid, 2-acrylamido-2,4,4-trimethylpentane-sulphonic acid, 2-methacrylamido-dodecyl-sulphonic acid, 2-acrylamido-2,6-dimethyl-3-heptane-sulphonic acid and partially or fully neutralized forms thereof.

As further examples, 2-acrylamido-2-methylpropane-sulphonic acid (AMPS), and partially or fully neutralized forms thereof, can be used.

The polymers of this class can for example be chosen from random amphiphilic polymers of AMPS modified by reaction with an n-monoalkylamine or a $C_6$-$C_{22}$ di-n-alkylamine, and such as those described in PCT Patent Application Publication No. WO00/31154. These polymers can also comprise other ethylenically unsaturated hydrophilic monomers chosen for example from the (meth)acrylic acids, their alkyl derivatives substituted at β or their esters obtained with monohydric alcohols or mono- or poly-alkylene glycols, (meth)acrylamides, vinylpyrrolidone, maleic anhydride, itaconic acid or maleic acid or mixtures thereof.

Exemplary polymers of this class are chosen from amphiphilic copolymers of AMPS and of at least one hydrophobic monomer with an ethylenic unsaturation.

These same copolymers can additionally comprise at least one ethylenically unsaturated monomer without a fatty chain, such as the (meth)acrylic acids, their alkyl derivatives substituted at β or their esters obtained with monohydric alcohols or mono- or poly-alkylene glycols, (meth)acrylamides, vinylpyrrolidone, maleic anhydride, itaconic acid or maleic acid or mixtures of these compounds.

These copolymers are, for example, described in European Patent Application No. A-750 899, U.S. Pat. No. 5,089,578 and in the following publications of Yotaro Morishima:

"Self-assembling amphiphilic polyelectrolytes and their nanostructures—Chinese Journal of Polymer Science Vol. 18, No. 40, (2000), 323-336."

"Micelle formation of random copolymers of sodium 2-(acrylamido)-2-methylpropanesulfonate and a non-ionic surfactant macromonomer in water as studied by fluorescence and dynamic light scattering—Macromolecules 2000, Vol. 33, No. 10-3694-3704";

"Solution properties of micelle networks formed by non-ionic moieties covalently bound to a polyelectrolyte: salt effects on rheological behavior—Langmuir, 2000, Vol. 16, No. 12, 5324-5332";

"Stimuli responsive amphiphilic copolymers of sodium 2-(acrylamido)-2-methylpropanesulfonate and associative macrornonomers—Polym. Preprint, Div. Polym. Chem. 1999, 40(2), 220-221".

The hydrophobic monomers with an ethylenic unsaturation of these copolymers are for example chosen from the acrylates and the acrylamides of the following formula (VIII):

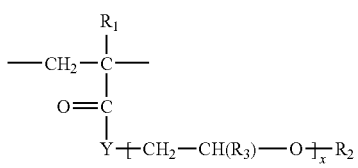

(VIII)

wherein $R_1$ and $R_3$, which may be identical or different, denote a hydrogen atom or a linear or branched $C_1$-$C_6$ alkyl radical (such as methyl); Y denotes O or NH; $R_2$ denotes a hydrophobic hydrocarbon radical having at least 8 or more carbon atoms such as from 8 to 22 carbon atoms and further such as from 8 to 18 carbon atoms and even further such as from 12 to 18 carbon atoms; x denotes the number of moles of alkylene oxide and varies from 0 to 100.

The radical $R_2$ is for example chosen from the linear $C_8$-$C_{18}$ alkyl radicals (for example n-hexyl, n-octyl, n-decyl, n-hexadecyl, n-dodecyl), branched or cyclic (for example cyclododecane ($C_{12}$) or adamantane ($C_{10}$)); the $C_6$-$C_{18}$ alkylperfluorinated radicals (for example the group of formula $(CH_2)_2$—$(CF_2)_9$—$CF_3$); the cholesteryl ($C_{27}$) radical or a cholesterol ester residue such as the cholesteryl oxyhexanoate group; and the polycyclic aromatic groups such as naphthalene or pyrene. Among these radicals, non-limiting mentions can be made of linear alkyl radicals and such as n-dodecyl radical.

According to at least one embodiment of the disclosure, the monomer of formula (VIII) has at least one alkylene oxide unit ($x \geq 1$) and for example a polyalkoxylated chain. The polyalkoxylated chain for example comprises ethylene oxide units and/or of propylene oxide units and for further example comprises ethylene oxide units. The number of alkoxylated units can generally vary from 3 to 100 and such as from 3 to 50 and further such as from 8 to 25.

Among these polymers, non-limiting mentions can be made of:

crosslinked or non-crosslinked, neutralized or non-neutralized copolymers having from 15 to 60 wt. % of AMPS units and from 40 to 85 wt. % of ($C_8$-$C_{16}$)alkyl(meth)acrylamide units or of ($C_8$-$C_{16}$)alkyl(meth)acrylate units relative to the polymer, such as those described in European Application No. 750 899;

terpolymers having from 10 to 90 mol. % of acrylamide units, from 0.1 to 10 mol. % of AMPS units and from 5 to 80 mol. % of n-($C_6$-$C_{18}$)alkylacrylamide units, such as those described in U.S. Pat. No. 5,089,578.

Non-limiting mentions can be made of the copolymers of fully neutralized AMPS and of dodecyl methacrylate as well as the non-crosslinked and crosslinked copolymers of AMPS and of n-dodecylmethacrylamide, such as those described in the articles by Morishima cited above.

Non-limiting mentions can also be made of the copolymers comprising 2-acrylamido-2-methylpropane-sulphonic acid (AMPS) units of the following formula (IX):

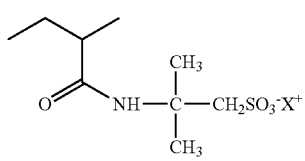

(IX)

wherein $X^+$ is a proton, an alkali metal cation, an alkaline-earth cation or the ammonium ion,
and units of the following formula (X):

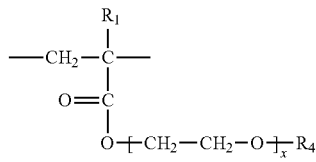

(X)

wherein x denotes an integer ranging from 3 to 100, such as from 3 to 50;

$R_1$ denotes a hydrogen atom or a linear or branched $C_1$-$C_6$ alkyl radical (such as methyl) and $R_4$ denotes a linear or branched $C_6$-$C_{22}$ alkyl and such as $C_{12}$-$C_{18}$ alkyl and further such as $C_{10}$-$C_{22}$ alkyl.

The polymers, for example, can bethose for which x=25, R1 denotes methyl and R4 represents n-dodecyl; they are described in the articles by Morishima mentioned above.

The concentration in mol. % of the units of formula (IX) and of the units of formula (X) can vary depending on the desired cosmetic application and the required rheological properties of the formulation. It can vary for example from 70 to 99 mol. % of AMPS units and from 1 to 30 mol. % of units of formula (X) relative to the copolymer and such as from 70 to 90 mol. % of AMPS units and from 10 to 30 mol. % of units of formula (X).

The polymers for which X+ denotes sodium or ammonium are exemplified.

Among the associative polymers of cationic type, non-limiting mention can be made of:

(I) the cationic associative polyurethanes which can be described in French Patent Application No. 0009609; it can be represented by the following general formula (XI):

R—X—(P)n-[L-(Y)m]r-L'-(P')p-X'—R' (XI)

wherein:

R and R', which may be identical or different, represent a hydrophobic group or a hydrogen atom;

X and X', which may be identical or different, represent a group bearing an amine function with or without a hydrophobic group, or else the group L";

L, L' and L", which may be identical or different, represent a group derived from a diisocyanate;

P and P', which may be identical or different, represent a group bearing an amine function with or without a hydrophobic group;

Y represents a hydrophilic group;

r is an integer ranging from 1 to 100, such as from 1 to 50 and further such as from 1 to 25, n, m, and p, each independently of one another, have a value ranging from 0 to 1000;

with the molecule comprising at least one protonated or quaternized amine function and at least one hydrophobic group.

Exemplary polyurethanes include those wherein the only hydrophobic groups are the groups R and R' at the chain ends.

Further exemplary cationic associative polyurethanes can be those corresponding to formula (XI) described above, wherein:

R and R' represent, both independently, a hydrophobic group,

X, X' each represent a group L', n and p have values ranging from 1 to 1000 and

L, L', L", which may be identical or different, represent a group derived from a diisocyanate;

P, P', which may be identical or different, represent a group bearing an amine function with or without a hydrophobic group Y represents a hydrophilic group;

and m has a value ranging from 0 to 1000. Exemplary cationic associative polyurethanes can also be those corresponding to formula (XI) above wherein:

R and R' represent, both independently, a hydrophobic group, X, X' each represent a group L", n and p have the value 0, L, L', L", which may be identical or different, represent a group derived from a diisocyanate, Y represents a hydrophilic group, and m has a value ranging from 0 to 1000.

The fact that n and p can have the value 0 signifies that these polymers may not have units derived from a monomer with an amine function, incorporated in the polymer during polycondensation. The protonated amine functions of these polyurethanes result from the hydrolysis of isocyanate functions, in excess, at the chain end, followed by alkylation of the primary amine functions formed by alkylating agents with a hydrophobic group, i.e. compounds of type RQ or R'Q, in which R and R' are as defined previously and Q denotes a leaving group such as a halide, a sulphate etc.

Exemplary cationic associative polyurethanes further can be those corresponding to formula (XI) above wherein:

R and R' represent, both independently, a hydrophobic group,

X and X' represent, both independently, a group having a quaternary amine, n and p have the value zero, and L and L', which may be identical or different, represent a group derived from a diisocyanate, Y represents a hydrophilic group, and m has a value ranging from 0 to 1000.

The number-average molecular weight of the cationic associative polyurethanes for example can range from 400 to 500,000, such as from 1,000 to 400,000 and further such as from 1,000 to 300,000.

"Hydrophobic group" is defined as previously

For example, the hydrophobic group can be derived from a fatty alcohol such as stearyl alcohol, dodecyl alcohol, decyl alcohol. It can also denote a hydrocarbon polymer, for example polybutadiene.

When X and/or X' denote a group bearing a tertiary or quaternary amine, X and/or X' can represent one of the following formulae:

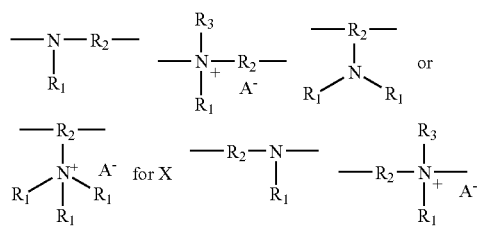

-continued

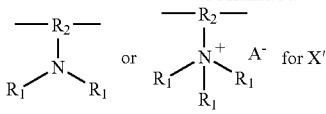

wherein:

$R_2$ represents an alkylene radical having from 1 to 20 carbon atoms, linear or branched, with or without a saturated or unsaturated ring, or an arylene radical, and at least one of the carbon atoms can be replaced with a heteroatom chosen from N, S, O, P;

$R_1$ and $R_3$, which may be identical or different, denote a linear or branched $C_1$-$C_{30}$ alkyl or alkenyl radical, an aryl radical, and at least one of the carbon atoms can be replaced with a heteroatom chosen from N, S, O, P;

$A^-$ is a physiologically acceptable counter-ion.

The groups L, L' and L" represent a group of formula:

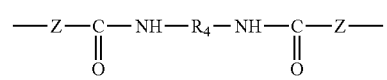

wherein:

Z represents —O—, —S— or —NH—; and $R_4$ represents an alkylene radical having from 1 to 20 carbon atoms, linear or branched, with or without a saturated or unsaturated ring, an arylene radical, and at least one of the carbon atom can be replaced with a heteroatom chosen from N, S, O and P.

The groups P and P', comprising an amine function, can represent at least one of the following formulae:

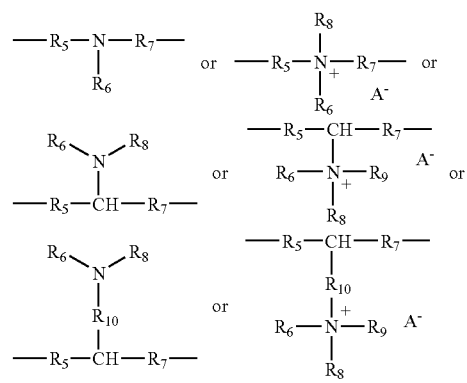

wherein:

$R_5$ and $R_7$, which can be identical or different, represent an alkylene radical having from 1 to 20 carbon atoms, linear or branched, with or without a saturated or unsaturated ring, or an arylene radical, and at least one of the carbon atoms can be replaced with a heteroatom chosen from N, S, O, P;

$R_6$, $R_8$ and $R_9$, which may be identical or different, denote a linear or branched $C_1$-$C_{30}$ alkyl or alkenyl radical, an aryl radical, and at least one of the carbon atoms can be replaced with a heteroatom chosen from N, S, O, P;

$R_{10}$ represents an alkylene group, linear or branched, optionally unsaturated, which can contain one or more heteroatoms selected from N, O, S and P, and $A^-$ is a physiologically acceptable counter-ion.

Regarding the meaning of Y, hydrophilic group means a water-soluble, polymeric or non-polymeric group.

As examples, mention can be made of non-polymeric, ethylene glycol, diethylene glycol and propylene glycol.

As further examples of hydrophilic polymer, mention can be made of the polyethers, the sulphonated polyesters, the sulphonated polyamides, or a mixture of these polymers. For example, the hydrophilic compound can be a polyether, such as a poly(ethylene oxide) or poly(propylene oxide).

The cationic associative polyurethanes of formula (XI) usable according to the disclosure can be formed from diisocyanates and various compounds possessing functions with a labile hydrogen. The functions with a labile hydrogen can be alcohol, primary or secondary amine or thiol functions giving, after reaction with the diisocyanate functions, respectively polyurethanes, polyureas and polythioureas. The term "polyurethanes" usable according to the present disclosure encompasses these three types of polymers, namely the polyurethanes proper, the polyureas and the polythioureas as well as copolymers of the latter.

The first type of compound involved in preparation of the polyurethane of formula (V) can be a compound having at least one unit with an amine function. This compound can be multifunctional, for example, the compound can be bifunctional, i.e., this compound can have two labile hydrogen atoms carried for example by a hydroxyl, primary amine, secondary amine or thiol function. A mixture of multifunctional and bifunctional compounds, wherein the percentage of multifunctional compounds is low, can also be used.

As stated previously, this compound can have more than one unit with an amine function. It is then a polymer with repetition of the unit with an amine function.

Compounds of this type can be represented by one of the following formulae:

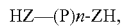

HZ—(P)n-ZH, or

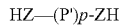

HZ—(P')p-ZH wherein Z, P, P', n and p are as defined previously.

As examples of compounds with an amine function, mentions can be made of N-methyldiethanolamine, N-tert-butyldiethanolamine, and N-sulphoethyldiethanolamine.

The second type of compound involved in preparation of the polyurethane of formula (XI) is a diisocyanate corresponding to the formula:

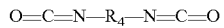

O═C═N—R₄—N═C═O wherein R₄ is defined above.

As examples, mentions can be made of methylenediphenyl-diisocyanate, and methylenecyclohexanediisocyanate, isophorone-diisocyanate, toluenediisocyanate, naphthalenediisocyanate, butanediisocyanate, hexanediisocyanate.

The third type of compound involved in preparation of the polyurethane of formula (XI) can be a hydrophobic compound intended to form the hydrophobic end groups of the polymer of formula (XI).

This type of compound can comprise a hydrophobic group and a functional group with a labile hydrogen, for example a hydroxyl, primary or secondary amine, or thiol.

As examples, this compound can be a fatty alcohol, such as stearyl alcohol, dodecyl alcohol, decyl alcohol. When this compound has a polymer chain, it can for example be hydrogenated alpha-hydroxyl polybutadiene.

The hydrophobic group of the polyurethane of formula (XI) can also be introduced through the reaction of quaternization of the tertiary amine of the compound having at least one tertiary amine unit. Thus, the hydrophobic group is introduced by the quaternizing agent. This quaternizing agent is a compound of type RQ or R'Q, wherein R and R' are as defined previously and Q denotes a leaving group such as a halide, a sulphate etc.

The cationic associative polyurethane can in addition comprise a hydrophilic sequence. This sequence is supplied by the fourth type of compound involved in preparation of the polymer. This compound can be multifunctional. It is, for example, bifunctional. It can also be a mixture, with a low percentage of multifunctional compounds.

The functional groups with a labile hydrogen are alcohol, primary or secondary amine, or thiol functions. This compound can be a polymer terminated at the chain ends by one of these functions with a labile hydrogen.

As examples, mentions can be made of non-polymeric ethylene glycol, diethylene glycol and propylene glycol.

If it is a hydrophilic polymer, non-limiting mentions can be made of the sulphonated polyesters, the sulphonated polyamides, or a mixture thereof. For example, the hydrophilic polymer is a polyether and such as a poly(ethylene oxide) or polypropylene oxide).

The hydrophilic group designated Y in formula (XI) is optional. In fact, the units with a quaternary amine or protonated function may be sufficient to provide the solubility or dispersibility in water necessary for this type of polymer in an aqueous solution.

Although the presence of a hydrophilic group Y is optional, cationic associative polyurethanes having such a group can also be used.

(II) the cationic polymer or polymers obtained by polymerization of a mixture of monomers comprising at least one vinylic monomer substituted with at least one amino group, at least one non-ionic hydrophobic vinylic monomer, and at least one associative vinylic monomer.

Among these cationic polymers, non-limiting mentions can be made of the compound marketed by the company NOVEON under the name AQUA CC, which corresponds to the INCI name POLYACRYLATE-1 CROSSPOLYMER.

POLYACRYLATE-1 CROSSPOLYMER is the product from polymerization of a mixture of monomers comprising:
a di($C_1$-$C_4$ alkyl)amino($C_1$-$C_6$ alkyl)methacrylate,
at least one ester of $C_1$-$C_{30}$ alkyl and (meth)acrylic acid,
a polyethoxylated $C_{10}$-$C_{30}$ alkyl methacrylate (20-25 moles of ethylene oxide units),
an allyl ether of polyethylene glycol/polypropylene glycol 30/5,
a hydroxy($C_2$-$C_6$ alkyl)methacrylate, and
an ethylene glycol dimethacrylate.

(III) the quaternized (cationic) alkylhydroxyethylcelluloses such as the products QUATRISOFT LM 200, QUATRISOFT LM-X 529-18-A, QUATRISOFT LM-X 529-18-B ($C_{12}$ alkyl) and QUATRISOFT LM-X 529-8 ($C_{18}$ alkyl) sold by the company AMERCHOL, the products CRODACEL QM, CRODACEL QL ($C_{12}$ alkyl) and CRODACEL QS ($C_{18}$ alkyl) sold by the company CRODA and the product SOFTCAT SL 100 sold by the company AMERCHOL.

Cationic polyvinyllactam polymers according to the disclosure.

The cationic poly(vinyllactam) polymers according to the disclosure comprise:
a) at least one monomer of the vinyllactam or alkylvinyllactam type; and
b) at least one monomer with the following structures (XII) or (XIII):

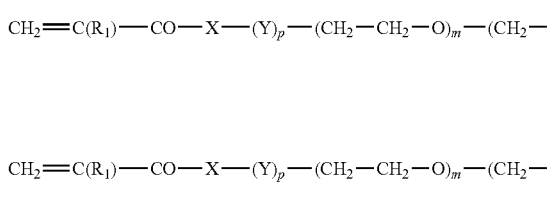

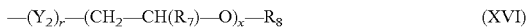

wherein:

X denotes an oxygen atom or a radical $NR_6$, $R_1$ and $R_6$ denote, independently of one another, a hydrogen atom or a linear or branched $C_1$-$C_5$ alkyl radical, $R_2$ denotes a linear or branched $C_1$-$C_4$ alkyl radical, $R_3$, $R_4$ and $R_5$ denote, independently of one another, a hydrogen atom, a linear or branched $C_1$-$C_{30}$ alkyl radical or a radical of formula (XIV):

$$—(Y_2)_r—(CH_2—CH(R_7)—O)_x—R_8 \quad (XVI)$$

$Y$, $Y_1$ and $Y_2$ denote, independently of one another, a linear or branched $C_2$-$C_{16}$ alkylene radical, $R_7$ denotes a hydrogen atom, or a linear or branched $C_1$-$C_4$ alkyl radical or a linear or branched $C_1$-$C_4$ hydroxyalkyl radical, $R_8$ denotes a hydrogen atom or a linear or branched $C_1$-$C_{30}$ alkyl radical, p, q and r denote, independently of one another, either the value zero, or the value 1, m and n denote, independently of one another, an integer ranging from 0 to 100, x denotes an integer ranging from 1 to 100, Z denotes an anion of organic or mineral acid, provided that:

at least one of the substituents $R_3$, $R_4$, $R_5$ or $R_8$ denotes a linear or branched $C_9$-$C_{30}$ alkyl radical, if m or n is different from zero, then q is equal to 1, if m or n is equal to zero, then p or q is equal to 0.

The cationic poly(vinyllactam) polymers according to the disclosure can be crosslinked or non-crosslinked and can also be block polymers.

For example, the Z-counter-ion of the monomers of formula (XII) is chosen from the halide ions, the phosphate ions, the methosulphate ion, and the tosylate ion.

For example, $R_3$, $R_4$ and $R_5$ denote, independently of one another, a hydrogen atom or a linear or branched $C_1$-$C_{30}$ alkyl radical.

For example, the monomer b) is a monomer of formula (XII) for which, for example, m and n are equal to zero.

The vinyl lactam or alkylvinyllactam monomer is for example a compound of structure (XV):

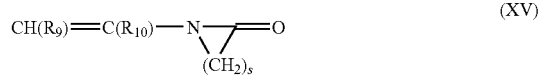

wherein:

s denotes an integer ranging from 3 to 6, $R_9$ denotes a hydrogen atom or a $C_1$-$C_5$ alkyl radical, $R_{10}$ denotes a hydrogen atom or a $C_1$-$C_5$ alkyl radical, provided that at least one of the radicals $R_9$ and $R_{10}$ denotes a hydrogen atom.

As an example, the monomer (XV) is vinylpyrrolidone.

The cationic poly(vinyllactam) polymers according to the disclosure can also contain at least one additional monomer, for example, cationic or non-ionic.

As examples of compounds according to the disclosure, mentions can be made of the following terpolymers comprising at least:

a) a monomer of formula (XV), b) a monomer of formula (XII) wherein p=1, q=0, $R_3$ and $R_4$ denote, independently of one another, a hydrogen atom or a $C_1$-$C_5$ alkyl radical and $R_5$ denotes a $C_9$-$C_{24}$ alkyl radical and c) a monomer of formula (XIII) wherein $R_3$ and $R_4$ denote, independently of one another, a hydrogen atom or a $C_1$-$C_5$ alkyl radical.

For example, the terpolymers can have, by weight, 40 to 95% of monomer (a), 0.1 to 55% of monomer (c) and 0.25 to 50% of monomer (b).

The polymers can be described in PCT Patent Application Publication No. WO 00/68282, the contents of which form an integral part of the disclosure.

For example, the vinylpyrrolidone/dimethylaminopropyl-methacrylamide/dodecyldimethylmethacrylami-dopropylammonium tosylate terpolymers, the vinylpyrrolidone/dimethylaminopropylmethacrylamide/cocoyldimethyl-methacrylamidopropylammonium tosylate terpolymers, the vinylpyrrolidone/dimethylaminopropyl-methacrylamide/lauryldimethylmethacrylami-dopropylammonium tosylate or chloride terpolymers, can be used as the cationic poly(vinyllactam) polymers according to the disclosure.

The amphoteric associative polymers are, for example, chosen from those having at least one non-cyclic cationic unit. For example, those prepared from or comprising 1 to 20 mol. % of fatty-chain monomer, and such as from 1.5 to 15 mol. % and further such as from 1.5 to 6 mol. %, relative to the total number of moles of monomers, can be used.

The amphoteric associative polymers that can be used according to the disclosure comprise, or are prepared by copolymerizing 1) at least one monomer of formula (XVI) or (XVII):

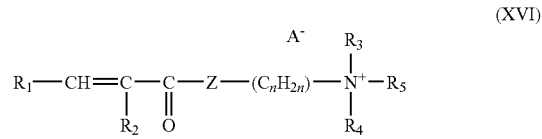

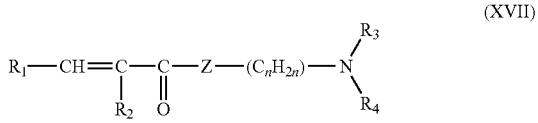

(XVII)

wherein $R_1$ and $R_2$, which may be identical or different, represent a hydrogen atom or a methyl radical, $R_3$, $R_4$ and $R_5$, which may be identical or different, represent a linear or branched alkyl radical having from 1 to 30 carbon atoms, Z represents a group NH or an oxygen atom, n is an integer ranging from 2 to 5, $A^-$ is an anion derived from an organic or mineral acid, such as a methosulphate anion or a halide such as chloride or bromide;

2) at least one monomer of formula (XVIII)

(XVIII)

wherein $R_6$ and $R_7$, which may be identical or different, represent a hydrogen atom or a methyl radical;

and 3) at least one monomer of formula (XIX):

(XIX)

wherein $R_6$ and $R_7$, which may be identical or different, represent a hydrogen atom or a methyl radical, X denotes an oxygen or nitrogen atom and $R_8$ denotes a linear or branched alkyl radical having from 1 to 30 carbon atoms;

at least one of the monomers of formula (XVI), (XVII) or (XIX) having at least one fatty chain.

The monomers of formula (XVI) and (XVII) are for example chosen from:

dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, dimethylaminopropyl methacrylamide, dimethylaminopropyl acrylamide, these monomers optionally being quaternized, for example by a $C_1$-$C_4$ alkyl halide or a $C_1$-$C_4$ dialkyl sulphate.

For example, the monomer of formula (XVI) can be chosen from acrylamidopropyl trimethyl ammonium chloride and methacrylamidopropyl trimethyl ammonium chloride.

The monomers of formula (XVIII) of the present disclosure are for example chosen from acrylic acid, methacrylic acid, crotonic acid and methyl-2 crotonic acid. For example, the monomer of formula (XVIII) is acrylic acid.

The monomers of formula (XIX) of the present disclosure are for example chosen from $C_{12}$-$C_{22}$ and such as $C_{16}$-$C_{18}$ alkyl acrylates and methacrylates.

The monomers of the amphoteric fatty-chain polymers of the disclosure are for example already neutralized and/or quaternized.

The ratio value of the number of cationic charges/anionic charges can be, for example, equal to about 1.

The amphoteric associative polymers of this class may comprise from 1 to 10 mol. % of the fatty-chain monomer (monomer of formula (XVI), (XVII) or (XIX)), and such as from 1.5 to 6 mol. %.

The amphoteric associative polymers of this class can also contain other monomers, such as non-ionic monomers and such as $C_1$-$C_4$ alkyl acrylates or methacrylates.

Amphoteric associative polymers according to the disclosure are for example described and prepared in PCT Patent Application No. WO 9844012.

Among the amphoteric associative polymers according to the disclosure, non-limiting mentions can be made of the acrylic acid/(meth)acrylamidopropyl trimethyl ammonium chloride/stearyl methacrylate terpolymers.

The associative polymers of the non-ionic type that can be used according to the disclosure are for example chosen from:

(a) the copolymers of vinyl pyrrolidone and of hydrophobic fatty-chain monomers, for example:

the products ANTARON V216® or GANEX V216® (vinylpyrrolidone/hexadecene copolymer) sold by the company I.S.P.

the products ANTARON V220® or GANEX V220® (vinylpyrrolidone/eicosene copolymer) sold by the company I.S.P.

(b) the copolymers of $C_1$-$C_6$ alkyl methacrylates or acrylates and of amphiphilic monomers having at least one fatty chain, for example the methyl acrylate/ethoxylated stearyl acrylate copolymer sold by the company GOLDSCHMIDT under the name ANTIL 208®.

(c) the copolymers of hydrophilic methacrylates or acrylates and of hydrophobic monomers having at least one fatty chain, for example the polyethylene glycol methacrylate/lauryl methacrylate copolymer.

(d) the polyether polyurethanes having in their chain, simultaneously, hydrophilic sequences most often of a polyethoxylated nature and hydrophobic sequences which can be aliphatic chains alone and/or cycloaliphatic and/or aromatic chains.

(e) the polymers with an aminoplast ether backbone possessing at least one fatty chain, such as the PURE THIX® compounds offered by the company SUD-CHEMIE.

(f) the celluloses or their derivatives, modified by groups having at least one fatty chain such as alkyl, aralkyl, alkaryl groups or mixtures thereof, where the alkyl groups are $C_8$- and for example:

the non-ionic alkylhydroxyethylcelluloses such as the products NATROSOL PLUS GRADE 330 CS and POLYSURF 67 ($C_{16}$ alkyl) sold by the company AQUALON the non-ionic nonoxynylhydroxyethylcelluloses such as the product AMERCELL HM-1500 sold by the company AMERCHOL;

the non-ionic alkylcelluloses such as the product BERMOCOLL EHM 100 sold by the company BEROL NOBEL; and (g) the associative guar derivatives such as the hydroxypropylguars modified by a fatty chain such as the product ESAFLOR HM 22 (modified by a $C_{22}$ alkyl chain) sold by the company LAMBERTI; the product MIRACARE XC 95-3 (modified by a $C_{14}$ alkyl chain) and the product RE 205-146 (modified by a $C_{20}$ alkyl chain) sold by RHODIA CHIMIE.

For example, the polyether polyurethanes have at least two lipophilic hydrocarbon chains, having from 6 to 30 carbon atoms, separated by a hydrophilic sequence, and the hydrocarbon chains can be pendant chains or chains at the end of the hydrophilic sequence. For example, it is possible that at least one pendant chain is envisaged. Moreover, the polymer can have a hydrocarbon chain at one end or at both ends of a hydrophilic sequence.

The polyether polyurethanes can be multiblock, such as in the form of a triblock. The hydrophobic sequences can be at each end of the chain (for example: triblock copolymer with hydrophilic central sequence) or distributed both at the ends and within the chain (multiblock copolymer, for example). These same polymers can also be grafts or in star form.

The non-ionic fatty-chain polyether polyurethanes can be triblock copolymers whose hydrophilic sequence is a polyethoxylated chain having from 50 to 1000 ethoxylated groups. The non-ionic polyether polyurethanes may have a urethane bond between the hydrophilic sequences, hence their name.

By extension, the non-ionic fatty-chain polyether polyurethanes may also include those whose hydrophilic sequences are bound to the lipophilic sequences by other chemical bonds.

As examples of non-ionic fatty-chain polyether polyurethanes usable in the disclosure, mentions can be made of RHEOLATE 205® with a urea function sold by the company RHEOX, RHEOLATES® 208, 204 and 212, and ACRYSOL RM 184®.

Non-limiting mentions can also be made of the product ELFACOS T210® with a $C_{12-14}$ alkyl chain and the product ELFACOS T212® with a $C_{18}$ alkyl chain from AKZO.

The product DW 1206B® from ROHM & HAAS with a $C_{20}$ alkyl chain and with a urethane bond, offered at 20% dry matter in water, can also be used.

Solutions or dispersions of these polymers such as in water or in an aqueous-alcoholic medium can also be used. As examples of such polymers, mentions can be made of RHEOLATE® 255, RHEOLATE® 278 and RHEOLATE® 244 sold by the company RHEOX. The products DW 1206F and DW 1206J offered by the company ROHM & HAAS can also be used.

The polyether polyurethanes usable according to the disclosure are for example those described in the article of G. Formum, J. Bakke and Fk. Hansen—Colloid Polym. Sci 271, 380-389 (1993).

Further non-limiting mentions can be made of a polyether polyurethane that can be obtained by polycondensation of at least three compounds comprising (i) at least one polyethylene glycol comprising from 150 to 180 moles of ethylene oxide, (ii) stearyl alcohol or decyl alcohol and (iii) at least one diisocyanate.

The polyether polyurethanes are for example sold by the company ROHM & HAAS under the names ACULYN 46® and ACULYN 44® [ACULYN 46® is a polycondensate of polyethylene glycol at 150 or 180 moles of ethylene oxide, of stearyl alcohol and of methylene bis(4-cyclohexyl-isocyanate) (SMDI), at 15 wt % in a matrix of maltodextrin (4%) and of water (81%); ACULYN 44® is a polycondensate of polyethylene glycol at 150 or 180 moles of ethylene oxide, of decyl alcohol and of methylene bis(4-cyclohexylisocyanate) (SMDI), at 35 wt. % in a mixture of propylene glycol (39%) and of water (26%)].

The polymeric thickener or thickeners for aqueous phase of the disclosure can be chosen from the associative and non-associative polymers with sugar units, the associative and non-associative acrylic and methacrylic anionic polymers, and the associative and non-associative polyurethanes.

Thickeners of the Oil Phase

In some embodiments, the polymers structurizing the oily phase via physical interactions are chosen from polyamides, siliconized polyamides, saccharide and polysaccharide mono- and poly-alkyl esters, amide derivatives of N-acylated amino acids, and copolymers comprising an alkylene or styrene block, and said copolymers can be diblock, triblock, multi-block, radial-block polymers, also called star copolymers, or alternatively comb polymers.

1) The polymers having at least one crystallizable sequence in their backbone.

There are also polymers that are soluble or dispersible in the oil or oily phase by heating above their melting point (m.p.). These polymers are for example block copolymers comprising at least 2 blocks of different chemical nature, one of which is crystallizable.

As polymers having at least one crystallizable block in their backbone, suitable for application of the disclosure, mentions can be made of:

i). The polymers defined in U.S. Pat. No. 5,156,911;

ii). The block copolymers of olefin or of cycloolefin with a crystallizable chain, such as those resulting from block polymerization of:

cyclobutene, cyclohexene, cyclooctene, norbornene (i.e. bicyclo(2,2,1)heptene-2), 5-methylnorbornene, 5-ethylnorbornene, 5,6-dimethyl-norbornene, 5,5,6-trimethyl norbornene, 5-ethylidene-norbornene, 5-phenylnorbornene, 5-benzylnorbornene, 5-vinylnorbornene, 1,4,5,8-dimethane-1,2,3,4,4a,5,8a-octahydronaphthalene, dicyclopentadiene, and mixtures thereof;

ethylene, propylene, 1-butene, 3-methyl-1-butene, 1-hexene, 4-methyl-1-pentene, 1-octene, 1-decene, 1-eicosene or mixtures thereof. These block copolymers can be for instance, (ethylene/norbornene) block copolymers and (ethylene/propylene/ethylidene-norbornene) block terpolymers.

It is also possible to use those resulting from the block copolymerization of at least two $C_2$-$C_{16}$ and for example $C_2$-$C_{12}$ α-olefins, such as those mentioned previously and for example the diblock polymers of ethylene and of 1-octene.

The copolymers may have at least one crystallizable block, the remainder of the copolymer being amorphous (at room temperature). These copolymers can, moreover, have two crystallizable blocks of different chemical nature. The copolymers may be those that have, simultaneously, at room temperature, a crystallizable block and an amorphous block, both hydrophobic and lipophilic, distributed sequentially; we may mention for example the polymers possessing at least one of the following crystallizable sequences and at least one of the following amorphous sequences:

Sequence that is naturally crystallizable: a) polyester such as poly(alkylene terephthalate), b) polyolefin such as polyethylenes or polypropylenes.

Sequence that is amorphous and lipophilic, such as the amorphous polyolefins or copoly(olefin)s such as poly (isobutylene), hydrogenated polybutadiene, hydrogenated poly(isoprene).

As examples of the copolymers with a crystallizable sequence and an amorphous sequence, mentions can be made of:

a) the poly(δ-caprolactone)-b-poly(butadiene) block copolymers, for example used in hydrogenated form, such as those described in the article "Melting behavior of poly(δ-caprolactone)-block-polybutadiene copolymers" of S. Nojima, Macromolecules, 32, 3727-3734 (1999).

b) the hydrogenated poly(butyleneterephthalate)-b-poly(isoprene) block or multiblock copolymers, mentioned in the article "Study of morphological and mechanical properties of PP/PBT" of B. Boutevin et al., Polymer Bulletin, 34, 117-123 (1995).

c) the poly(ethylene)-b-copoly(ethylene/propylene) block copolymers mentioned in the articles "Morphology of semi-crystalline block copolymers of ethylene-(ethylene-alt-propylene)" of P. Rangarajan et al., Macromolecules, 26, 4640-4645 (1993), and "Polymer aggregates with crystalline cores: the system poly(ethylene)-poly(ethylene-propylene)" of P. Richter et al., Macromolecules, 30, 1053-1068 25 (1997).

d) the poly(ethylene)-b-poly(ethylethylene) block copolymers mentioned in the general article "Crystallization in block copolymers" of I. W. Hamley, Advances in Polymer Science, Vol. 148, 113-137 (1999).

The semi-crystalline polymers usable according to the disclosure can be non-crosslinked or partially crosslinked, since the degree of crosslinking does not interfere with their dissolution or dispersion in the liquid oily phase by heating above their melting point. It can then be a chemical crosslinking, by reaction with a multifunctional monomer during polymerization. It can also be a physical crosslinking, which can then be due either to the establishment of bonds of the hydrogen or bipolar type between groups carried by the polymer, for example bipolar interactions between carboxylate ionomers, the interactions being of a small amount and carried by the backbone of the polymer; or to phase separation between the crystallizable blocks and the amorphous blocks carried by the polymer.

For example, in some embodiments the semi-crystalline polymers that are suitable for the disclosure are non-crosslinked.

As examples of semi-crystalline polymer usable in the composition according to the disclosure, mentions can be made of the products INTELIMER® from the company Landec described in the brochure "INTELIMER® polymers". These polymers are in solid form at room temperature (25° C.). They bear crystallizable side chains and have the monomer as defined in the preceding formula X. Non-limiting mention can also be made of "LANDEC IP22®", having a melting point m.p. of 56° C., which is a product that is viscous at room temperature, impermeable, non-sticky.

It is also possible to use the semi-crystalline polymers described in examples 3, 4, 5, 7, 9 of U.S. Pat. No. 5,156,911, obtained from the copolymerization of acrylic acid and $C_5$ to $C_{16}$ alkyl(meth)acrylate such as those obtained from the copolymerization:
of acrylic acid, of hexadecylacrylate and of isodecylacrylate in the proportions 1/16/3,
of acrylic acid and of pentadecylacrylate in the proportions 1/19,
of acrylic acid, of hexadecylacrylate, and of ethylacrylate in the proportions 2.5/76.5/20,
of acrylic acid, of hexadecylacrylate and of methylacrylate in the proportions 5/85/10, or
of acrylic acid and octadecylmethacrylate in the ratio 2.5/97.5.

It is also possible to use the polymer "Structure O" marketed by the company National Starch, such as that described in U.S. Pat. No. 5,736,125, of m.p. 44° C., as well as the crystallizable semi-crystalline polymers with pendant chains with fluorinated groups as described in examples 1, 4, 6, 7 and 8 of PCT Patent Application Publication No. WO 01/19333.

It is also possible to use the semi-crystalline polymers obtained by copolymerization of stearyl acrylate and of acrylic acid or of NVP or by copolymerization of behenyl acrylate and of acrylic acid or of NVP, as described in U.S. Pat. No. 5,519,063 or European Patent Application Publication No. 0 550 745.

According to at least one embodiment, the semi-crystalline polymers suitable for application of the present disclosure are for example the alkylated acrylates, among which mentions can be made of the copolymers from LANDEC:
DORESCO IPA 13-1®: poly(stearyl acrylate), m.p. of 49° C. and MW of 145000;
DORESCO IPA 13-3®: poly(acrylate/methacrylic acid), m.p. of 65° C. and MW of 114000;
DORESCO IPA 13-4®: poly(acrylate/vinyl pyrrolidone), m.p. of 44° C. and MW of 387000;
DORESCO IPA 13-5®: poly(hydroxyethyl acrylate/methacrylate), m.p. of 47° C. and MW of 397600;
DORESCO IPA 13-6®: poly(behenyl acrylate), m.p. of 66° C.

The Non-Siliconized Polyamides

The polyamides that can be used for the present disclosure are for example those described in U.S. Pat. No. 5,783,657 of the company UNION CAMP. The section of U.S. Pat. No. 5,783,657 discussing these polymers is incorporated by reference.

Each of these polyamides, for example, satisfies the following formula:

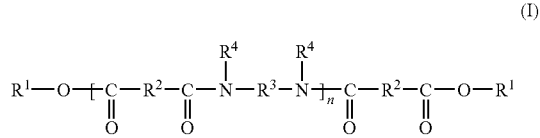

(I)

wherein n denotes a whole number of amide units such that the number of ester groups represents from 10 to 50% of the total number of ester and amide groups;

$R^1$ is, independently at each occurrence, an alkyl or alkenyl group having at least 4 carbon atoms and for example from 4 to 24 carbon atoms;

$R^2$ represents, independently at each occurrence, a $C_4$ to $C_{55}$ hydrocarbon group provided that at least 50% of the groups $R^2$ represent a $C_{30}$ to $C_{55}$ hydrocarbon group;

$R^3$ represents, independently at each occurrence, an organic group provided with at least 2 carbon atoms, hydrogen atoms and optionally with at least one oxygen or nitrogen atom; and $R^4$ represents, independently at each occurrence, a hydrogen atom, a $C_1$ to $C_{10}$ alkyl group or a direct bond to $R^3$ or to another $R^4$ so that the nitrogen atom to which $R^3$ and $R^4$ are bound simultaneously forms part of a heterocyclic structure defined by $R^4$—N—$R^3$, with at least 50% of the $R^4$ representing a hydrogen atom. For example, the ester groups of this polyamide represent from 15 to 40% of the total number of ester and amide groups and such as from 20 to 35%. Moreover, n can represent an integer ranging from 1 to 10, and such as from 1 to 5, inclusively.

For example, $R^1$ is a $C_{12}$ to $C_{22}$ and such as a $C_{16}$ to $C_{22}$ alkyl group. In some embodiments $R^2$ can be a $C_{10}$ to $C_{42}$ hydrocarbon group (alkylene). In at least one embodiment, at least 50% and such as at least 75% of the $R^2$ are groups having from 30 to 42 carbon atoms. The other $R^2$ are $C_4$ to $C_{19}$ and such as $C_4$ to $C_{12}$ hydrogenated groups. $R^3$ can represent a $C_2$ to $C_{36}$ hydrocarbon group or a polyalkoxylated group and $R^4$ can represent a hydrogen atom. For example, $R^3$ represents a $C_2$ to $C_{12}$ hydrocarbon group. The hydrocarbon groups can be linear, cyclic or branched, saturated or unsaturated groups. Moreover, the alkyl and alkylene groups can be linear or branched, saturated or unsaturated groups.

The thickening of the liquid oil phase can be achieved via at least one polyamide as defined above. For example, these polyamides can be in the form of mixtures, and these mixtures can also contain at least one synthetic product corresponding to a polyamide as defined above with n having the value 0, i.e. a diester.

As structurizing polyamides usable in the disclosure, mentions can be made of the polyamide resins obtained from the condensation of an aliphatic dicarboxylic acid and a diamine (including the compounds having more than two carbonyl groups and two amine groups), the carbonyl and amine groups of adjacent single units being condensed by an amide bond. These polyamide resins can be those marketed under the brand VERSAMID® by the companies General Mills, Inc. and Henkel Corp., under the brand ONAMID® such as Onamid S or C. These resins have a number-average molecular weight in the range from 6000 and 9000. For more information on these polyamides, reference may be made to U.S. Pat. Nos. 3,645,705 and 3,148,125. As a further example, VERSAMID® 30 or 744 can be used.

It is also possible to use the polyamides sold or manufactured by the company Arizona under the reference names Uni-Rez (2658, 2931, 2970, 2621, 2613, 2624, 2665, 1554, 2623, 2662) and the product sold under the reference name Macramelt 6212 by the company Henkel. More information on these polyamides can be found in U.S. Pat. No. 5,500,209.

As examples of structurizing polyamides usable in the composition according to the disclosure, mentions can be made of the commercial products sold or manufactured by the company Arizona Chemical under the names Uniclear 80 and Uniclear 100. They are sold respectively in the form of gel at 80% (of active substance) and at 100% (of active substance) in a mineral oil. They have a softening point from 88 to 105° C. These commercial products are a mixture of copolymer of a $C_{36}$ diacid condensed on ethylene diamine, with average molecular weight of about 6,000. The ester end groups result from the esterification of the remaining acid terminations by cetyl alcohol, stearyl alcohol or mixtures thereof (also called cetylstearyl alcohol).

The Siliconized Polyamides

The polymers (homopolymers or copolymers) of siliconized polyamide type, suitable for application of the disclosure, have an average molecular weight ranging from 500 to 500,000, and possess at least one group comprising:

at least one polyorganosiloxane group, having from 1 to 1000 organosiloxane units, in the chain of the group or in the form of a graft, and at least two groups capable of establishing hydrogen interactions, chosen from the ester, amide, sulphonamide, carbamate, thiocarbamate, urea, thiourea, oxamido, guanidino, biguanidino groups, and combinations thereof, provided that at least one of these groups is different from an ester group, the polymer being solid at room temperature and soluble in the oily phase at a temperature ranging from 25 to 120° C.

The polymers of siliconized polyamide type suitable for application of the disclosure, and used as oil structurizing agent, can be chosen from:

polyorganosiloxanes comprising at least two groups capable of establishing hydrogen interactions, these two groups being arranged in the polymer chain, and, polyorganosiloxanes comprising at least two groups capable of establishing hydrogen interactions, these two groups being arranged on grafts or branchings.

The polymers of the siliconized polyamide type having two groups capable of establishing hydrogen interactions in the polymer chain can be polymers comprising at least one unit corresponding to the first formula below:

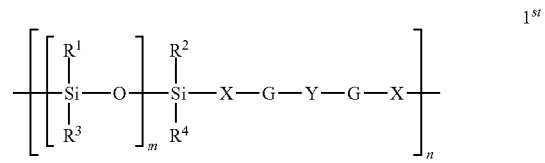

wherein:

1. $R^1$, $R^2$, $R^3$ and $R^4$, which may be identical or different, represent a group chosen from:

linear, branched or cyclic, $C_1$ to $C_{40}$ hydrocarbon groups, saturated or unsaturated, which optionally comprises at least one atom chosen from oxygen, sulphur and nitrogen atoms in their chain, and which can be substituted partly or completely with fluorine atoms, $C_6$ to $C_{10}$ aryl groups, optionally substituted with at least one $C_1$ to $C_4$ alkyl group, and polyorganosiloxane chains optionally comprising at least one atom chosen from oxygen, sulphur and nitrogen atoms;

2. X, which may be identical or different, represents a linear or branched $C_1$ to $C_{30}$, di-yl alkylene group, which optionally comprises at least one atom chosen from oxygen and nitrogen atoms in its chain;

3. Y is a linear or branched divalent alkylene, arylene, cycloalkylene, alkylarylene or arylalkylene group, saturated or unsaturated, $C_1$ to $C_{50}$, which optionally comprises at least one atom chosen from oxygen, sulphur and nitrogen atoms, and/or optionally comprises as substituent at least one atom or group chosen from fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl, $C_1$ to $C_3$ hydroxyalkyl and $C_1$ to $C_6$ alkylamino groups, or 4. Y represents a group corresponding to the formula:

wherein:

T represents a trivalent or tetravalent, linear or branched, saturated or unsaturated, $C_3$ to $C_{24}$ hydrocarbon group optionally substituted with a polyorganosiloxane chain, and which can comprise at least one atom chosen from O, N and S, or T represents a trivalent atom chosen from N, P and Al, and $R^5$ represents a linear or branched $C_1$ to $C_{50}$ alkyl group, or a polyorganosiloxane chain, which optionally comprises at least one group chosen from ester, amide, urethane, thiocarbamate, urea, thiourea and sulphonamide groups which may or may not be bound to another chain of the polymer, 5. G, which may be identical or different, represents the divalent groups chosen from:

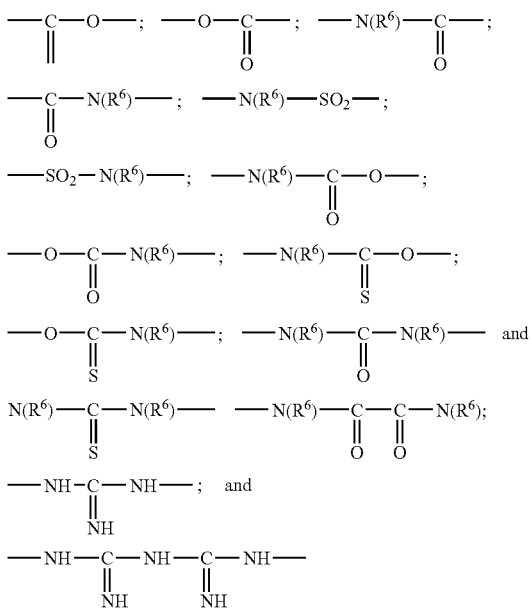

where $R^6$ represents a hydrogen atom or a linear or branched, $C_1$ to $C_{20}$ alkyl group, 6. n is an integer ranging from 2 to 500, such as from 2 to 200, and m is an integer ranging from 1 to 1000, such as from 1 to 700 and further such as from 6 to 200.

According to at least one embodiment, 80% of the $R^1$, $R^2$, $R^3$ and $R^4$, of the polymer can for example be chosen from methyl, ethyl, phenyl and 3,3,3-trifluoropropyl groups.

According to at least one embodiment, Y can represent various divalent groups, optionally having additional one or two free valences for establishing bonds with other units of the polymer or copolymer. Notably, Y can represent a group chosen from:

a) linear $C_1$ to $C_{20}$, such as $C_1$ to $C_{10}$, alkylene groups;

b) branched alkylene groups which can have rings and unconjugated, $C_{30}$ to $C_{56}$ unsaturations;

c) $C_5$-$C_6$ cycloalkylene groups;

d) phenylene groups optionally substituted with at least one $C_1$ to $C_{40}$ alkyl group;

e) $C_1$ to $C_{20}$ alkylene groups, having from 1 to 5 amide groups;

f) $C_1$ to $C_{20}$ alkylene groups, having at least one substituent, chosen from hydroxyl groups, $C_3$ to $C_8$ cycloalkane, $C_1$ to $C_3$ hydroxyalkyl and $C_1$ to $C_6$ alkylamines;

g) polyorganosiloxane chains of the formula:

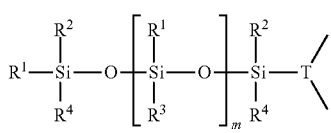

wherein $R^1$, $R^2$, $R^3$ and $R^4$, T and m are as defined above; and h) the polyorganosiloxane chains of formula:

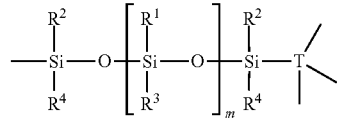

wherein $R^1$, $R^2$, $R^3$ and $R^4$, T and m are as defined above.

The polyorganosiloxanes of the second class can be polymers comprising at least one unit corresponding to the second formula below:

(II)

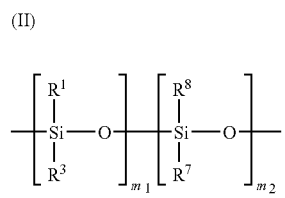

wherein:

$R^1$ and $R^3$, which may be identical or different, are as defined above for the preceding 1st formula;

$R^7$ represents a group as defined above for $R^1$ and $R^3$, or represents the group of formula —X-G-$R^9$ in which X and G are as defined above for the preceding 1st formula and $R^9$ represents a hydrogen atom or a linear, branched or cyclic, saturated or unsaturated, $C_1$ to $C_{50}$ hydrocarbon group, optionally comprising in its chain at least one atom chosen from O, S and N, optionally substituted with at least one fluorine atom and/or at least one hydroxyl group, or a phenyl group optionally substituted with at least one $C_1$ to $C_4$ alkyl group;

$R^8$ represents the group of formula —X-G-$R^9$ wherein X, G and $R^9$ are as defined above;

$m_1$ is an integer ranging from 1 to 998; and $m_2$ is an integer ranging from 2 to 500.

According to the disclosure, the siliconized polyamide used as structurizing agent can be a homopolymer, i.e. a polymer having several identical units, for example units according to the formulae defined previously.

According to the disclosure, it is also possible to use a siliconized polyamide comprising a copolymer having several different units according to the first formula above, i.e. a polymer wherein at least one of $R^1$, $R^2$, $R^3$, $R^4$, G, Y, m and n is different in one of the units. The copolymer can also be formed from several units according to the second formula above, wherein at least one of the $R^1$, $R^3$, $R^7$, $R^8$, $m_1$ and $m_2$ is different in at least one of the units.

It is also possible to use a copolymer having at least one unit according to the first formula and at least one unit according to the second formula, and the units according to the first formula and the units according to the second formula may be identical to or different from one another.

According to at least one embodiment, it is also possible to use a siliconized polyamide of the copolymer type additionally comprising at least one hydrocarbon unit having two groups capable of establishing hydrogen interactions chosen from ester, amide, sulphonamide, carbamate, thiocarbamate, urea, thiourea groups and combinations thereof. These copolymers can be block copolymers, sequence copolymers or graft copolymers.

According to at least one embodiment, the groups capable of establishing hydrogen interactions are amide groups of formula —C(O)NH— and —HN—C(O)—. In this case, the gelling agent can be, for example, a polymer comprising at least one unit according to the third or fourth formula below:

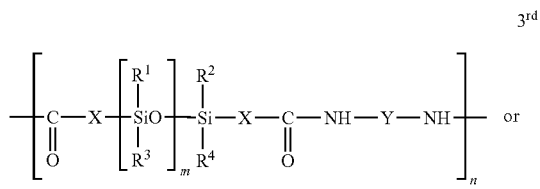

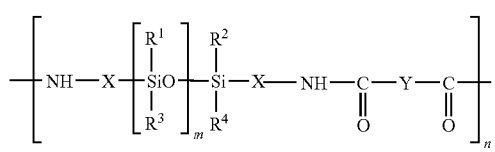

wherein $R^1$, $R^2$, $R^3$, $R^4$, X, Y, m and n are as defined previously.

In the polyamides according to the third and fourth formulae presented above:

m is an integer ranging from 1 to 700, such as from 15 to 500 and further such as from 15 to 45, and n is an integer ranging from 1 to 500, such as from 1 to 100 and further such as from 4 to 25, X is a linear or branched alkylene chain having from 1 to 30 carbon atoms, such as from 3 to 10 carbon atoms, and Y is a linear or branched alkylene chain or can comprise rings and/or unsaturations having from 1 to 40 carbon atoms, such as from 1 to 20 carbon atoms, and further such as from 2 to 6 carbon atoms, even further such as 6 carbon atoms.

In the third and fourth formulae presented above, the alkylene group representing X or Y can optionally comprise in its alkylene moiety at least one element chosen from:

1) 1 to 5 amide, urea or carbamate groups,
2) a $C_5$ or $C_6$ cycloalkyl group, and
3) a phenylene group optionally substituted with 1 to 3 $C_1$ to $C_3$ alkyl groups, which may be identical or different.

In the third and fourth formulae presented above, the alkylene groups can also be substituted with at least one element chosen from:

a hydroxyl group, a $C_3$ to $C_8$ cycloalkyl group, one to three $C_1$ to $C_{40}$ alkyl groups, a phenyl group optionally substituted with one to three $C_1$ to $C_3$ alkyl groups, a $C_1$ to $C_3$ hydroxyalkyl group, and a $C_1$ to $C_6$ aminoalkyl group.

In the third and fourth formulae presented above, Y can also represent:

wherein $R^5$ represents a polyorganosiloxane chain, and T represents a group of formula:

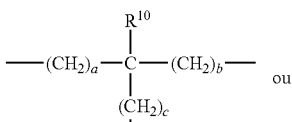

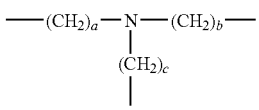

wherein a, b and c are, independently, integers in the range from 1 to 10, and $R^{10}$ is a hydrogen atom or a group such as those defined for $R^1$, $R^2$, $R^3$, $R^4$.

In the third and fourth formulae presented above, $R^1$, $R^2$, $R^3$, $R^4$ can represent, independently, a linear or branched $C_1$ to $C_{40}$ alkyl group, such as a $CH_3$, $C_2H_5$, n-$C_3H_7$ or isopropyl group, a polyorganosiloxane chain or a phenyl group optionally substituted with one to three methyl or ethyl groups.

As discussed above, the polymer can also comprise units according to the third or fourth formula presented above, which may be identical or different.

Thus, the polymer can be a siliconized polyamide containing several units according to the third or fourth formula presented above of different lengths, i.e. a polyamide corresponding to the fifth formula below:

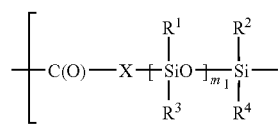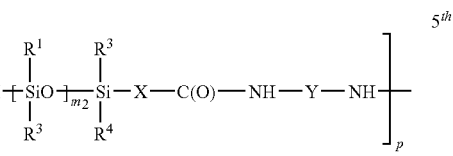

wherein X, Y, n, $R^1$ to $R^4$ have the meanings given previously, $m_1$ and $m_2$, which are different, are intergers ranging from 1 to 1000, and p is an integer ranging from 2 to 300.

In this formula, the units can be structured to form either a block copolymer, or a random copolymer, or an alternating copolymer. In this copolymer, the units can be not only of different lengths but also of different chemical structures, for example having different Y. In this case, the copolymer can correspond to the sixth formula:

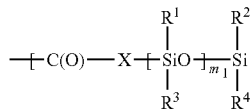 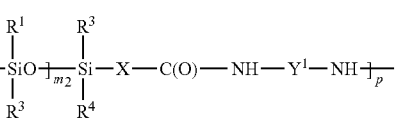

wherein $R^1$ to $R^4$, X, Y, $m_1$, $m_2$, n and p have the meanings given above and $Y_1$ is different from Y, but is chosen from the groups defined for Y. As previously discussed, the various units can be structured to form either a block copolymer, or a random copolymer, or an alternating copolymer.

According to at least one embodiment of the disclosure, the gelling siliconized polyamide can comprise a graft copolymer. Thus, the polyamide with silicone units can be grafted and optionally crosslinked by silicone chains with amide groups. Such polymers can be synthesized with trifunctional amines.

In this case, the copolymer can comprise at least one unit according to the seventh formula below:

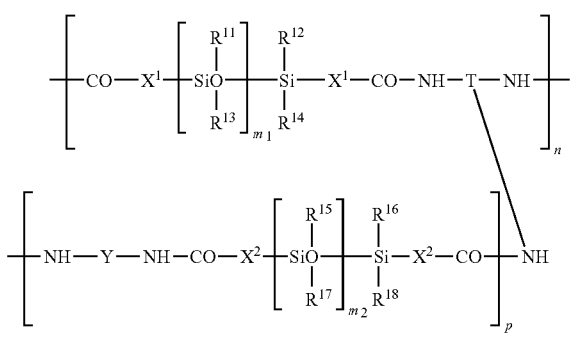

wherein $X^1$ and $X^2$, which may be identical or different, have the meaning given for X in the first formula above, n is as defined in the first formula above, Y and T are as defined in the first formula above, $R^{11}$ to $R^{18}$ are groups chosen from the same group as for $R^1$ to $R^4$, $m_1$ and $m_2$ are integers ranging from 1 to 1000, and p is an integer ranging from 2 to 500.

In the seventh formula presented above, in some embodiments:

p ranges from 1 to 25, such as from 1 to 7, $R^{11}$ to $R^{18}$ are methyl groups, T corresponds to one of the following formulae:

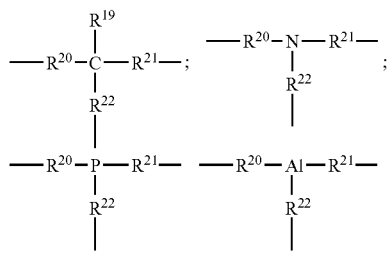

wherein $R^{19}$ is a hydrogen atom or a group chosen from the groups defined for $R^1$ to $R^4$, and $R^{20}$, $R^{21}$ and $R^{22}$ are, independently, linear or branched alkylene groups, T corresponds, for example, to the formula:

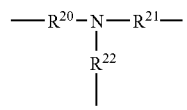

for example with $R^{20}$, $R^{21}$ and $R^{22}$ representing —$CH_2$—$CH_2$—, $m_1$ and $m_2$ are integers ranging from 15 to 500, or from 15 to 45, $X^1$ and $X^2$ represent —$(CH_2)_{10}$—, and Y represents —$CH_2$—.

These polyamides with a grafted silicone unit according to the seventh formula presented above can be copolymerized with silicone-polyamides according to the second formula to form block copolymers, alternating copolymers or random copolymers. The percentage by weight of grafted silicone units according to the seventh formula in the copolymer can range from 0.5 to 30 wt. %.

According to at least one embodiment, the siloxane units can be in the main chain or backbone of the polymer, but they can also be present in grafted or pendant chains. In the main chain, the siloxane units can be in the form of segments as described above. In the pendant or grafted chains, the siloxane units can appear individually or in segments.

According to at least one embodiment of the disclosure, the polyamides based on siloxanes can for example be:

the polyamides according to the third formula presented above where m is from 15 to 50;

mixtures of two or more polyamides in which at least one polyamide has a value of m in the range from 15 to 50 and at least one polyamide has a value of m in the range from 30 to 50; polymers according to the fifth formula described previously with $m_1$ selected in the range from 15 to 50 and $m_2$ selected in the range from 30 to 500 with the part corresponding to $m_1$ representing 1 to 99 wt. % of the total weight of the polyamide and the part corresponding to $m_2$ representing 1 to 99 wt. % of the total weight of the polyamide;

polyamide mixtures according to the third formula described previously combining:

1) 80 to 99 wt. % of a polyamide where n is equal to 2 to 10, such as from 3 to 6, and 2) 1 to 20% of a polyamide where n is ranging from 5 to 500, such as from 6 to 100;

polyamides corresponding to the sixth formula presented above where at least one of the Y and $Y^1$ contains at least one hydroxyl substituent;

polyamides according to the third formula synthesized with at least one part of an activated diacid (chloride, dianhydride or diester of diacid) instead of the diacid;

polyamides according to the third formula where X represents —$(CH_2)_3$— or —$(CH_2)_{10}$; or polyamides according to the third formula where the polyamides are terminated by a monofunctional chain chosen from monofunctional amines, monofunctional acids, monofunctional alcohols, including the fatty acids, the fatty alcohols and the fatty amines, for example octylamine, octanol, stearic acid and stearyl alcohol.

According to at least one embodiment of the disclosure, the chain ends of the polymer can be terminated with:
a $C_1$ to $C_{50}$ alkyl ester group by introducing a $C_i$ to $C_{50}$ monohydric alcohol during synthesis, and/or
a $C_1$ to $C_{50}$ alkyl amide group by using, as stopper, a monoacid if the silicone is alpha, omega-diaminated, or a monoamine if the silicone is alpha, omega-dicarboxylic acid.

According to at least one embodiment of the disclosure, it is possible to use a copolymer of silicone polyamide and of hydrocarbon polyamide, i.e. a copolymer having units according to the third or the fourth formula and polyamide hydrocarbon units. In this case, the silicone polyamide units can be arranged at the ends of the hydrocarbon polyamide.

Gelling agents based on polyamide containing silicones can be produced by silylic amidation of polyamides based on fatty acid dimer. This approach involves the reaction of free acid sites present on a polyamide as terminal sites, with oligosiloxanes-monoamines and/or oligosiloxanes-diamines (amidation reaction), or alternatively with oligosiloxane alcohols or oligosiloxane diols (esterification reaction). The esterification reaction may require the presence of acid catalysts, as is known by a person skilled in the art. The polyamide having free acid sites, used for the amidation or esterification reaction, may have a relatively high number of acid terminations (for example polyamides having high acid numbers, for example from 15 to 20).

For the amidation of the free acid sites of the hydrocarbon polyamides, diamine siloxanes with 1 to 300, such as 2 to 50, and further such as 2, 6, 9, 5, 12, 13, 5, 23 or 31 siloxane groups, can be used for the reaction with hydrocarbon polyamides based on fatty acid dimers. As further examples, diamine siloxanes having 13.5 siloxane groups can be used, and the siloxane-diamine having 13.5 siloxane groups and polyamides containing high levels of carboxylic acid end groups can also be used.

The reactions can be carried out in xylene for extracting the water produced from the solution by azeotropic distillation, or at higher temperatures (around 180 to 200° C.) without solvent. The effectiveness of the amidation and the degrees of reaction may decrease when the siloxane diamine is longer, i.e. when the number of siloxane groups is higher. Free amine sites can be blocked after the initial amidation reaction of the diaminosiloxanes by reacting them either with an acid siloxane, or with an organic acid such as benzoic acid.

For esterification of the free acid sites on the polyamides, this can be carried out in boiling xylene with about 1 wt. %, relative to the total weight of the reactants, of paratoluenesulphonic acid as catalyst.

These reactions carried out on the carboxylic acid end groups of the polyamide lead to the incorporation of silicone units only at the ends of the polymer chain.

As examples, mentions can be made of DC2-8178 Gellant and DC2-8179 Gellant from Dow Corning.

The Mono- or Polyalkyl Esters of Saccharide or Polysaccharide

Among the mono- or polyalkyl esters of saccharide or of polysaccharide suitable for application of the disclosure, non-limiting mentions can be made of the alkyls or polyalkyl esters of dextrin or of inulin.

For example, it can be a mono- or poly-ester of dextrin and of at least one fatty acid and for example corresponding to the following formula:

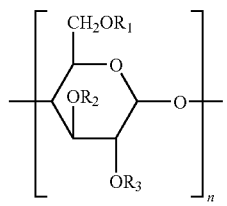

wherein:
n is an integer ranging from 3 to 200, such as from 20 to 150, and further such as from 25 to 50,
the radicals $R_1$, $R_2$ and $R_3$, which may be identical or different, are chosen from hydrogen and an acyl group (R—CO—) wherein the radical R is a linear or branched, saturated or unsaturated hydrocarbon group, having from 7 to 29, such as from 7 to 21, further such as from 11 to 19, even further such as from 13 to 17, or even 15, carbon atoms, provided that at least one of said radicals $R_1$, $R_2$ or $R_3$ is different from hydrogen.

For example, $R_1$, $R_2$ and $R_3$ can represent hydrogen or an acyl group (R—CO—) wherein R is a hydrocarbon group as defined previously, provided that at least two of said radicals $R_1$, $R_2$ or $R_3$ are identical and different from hydrogen.

All of the radicals $R_1$, $R_2$ and $R_3$ can represent an acyl group (R—CO) that is identical or different, and for example identical.

For example, n varies from 25 to 50, and such as is equal to 38 in the general formula of the saccharide ester usable in the present disclosure.

For example, when the radicals $R_1$, $R_2$ and/or $R_3$, which may be identical or different, represent an acyl group (R—CO), they can be chosen from caprylic, capric, lauric, myristic, palmitic, stearic, arachic, behenic, isobutyric, isovaleric, ethyl-2 butyric, ethylmethylacetic, isoheptanoic, ethyl-2 hexanoic, isononanoic, isodecanoic, isotridecanoic, isomyristic, isopalmitic, isostearic, isoarachic, isohexanoic, decenoic, dodecenoic, tetradecenoic, myristoleic, hexadecenoic, palmitoleic, oleic, elaidic, asclepinic, gondoleic, eicosenoic, sorbic, linoleic, linolenic, punicic, stearidonic, arachidonic, stearol radicals, and mixtures thereof.

For example, at least one dextrin palmitate is used as ester of dextrin and of fatty acid(s). It can be used alone or mixed with other esters.

For further example, the ester of dextrin and of fatty acid has a degree of substitution less than or equal to 2.5 based on one glucose unit, for example varying from 1.5 to 2.5, such as from 2 to 2.5. The weight-average molecular weight of the ester of dextrin can be for example from 10,000 to 150,000, such as from 12,000 to 100,000 and further such as from 15,000 to 80,000.

Esters of dextrin, such as dextrin palmitates, are available commercially under the name RHEOPEARL TL or RHEOPEARL KL from the company Chiba Flour.

Amide Derivatives of N-Acylated Amino Acids

The amides of N-acylated amino acids that can be used are for example the diamides of the combination of an N-acylamino acid with amines having from 1 to 22 carbon atoms, such as those described in French Patent No. 2 281 162. They are for example the amide derivatives of alkyl glutamic acid such as the dibutylamide of laurylglutamic acid, marketed by the company Ajinomoto under the name "Gelling agent GP-1" or else the dibutylamide of 2-ethylhexanoyl glutamic acid marketed by the company Ajinomoto under the name "Gelling agent GA-01".

Copolymers Comprising an Alkylene or Styrene Block

The copolymers can have a comb or block structure of the diblock, triblock, multi-block and/or radial or star type and can have at least two segments that are thermodynamically incompatible.

The structurizing agent can comprise, for example, a styrene segment block as described in European Application No. 0 497 144, PCT Patent Application Publication No. WO 98/42298, and U.S. Pat. Nos. 6,225,690, 6,174,968, and 6,225,390, an ethylene/butylene segment, an ethylene/propylene segment as described in U.S. Pat. Nos. 6,225,690, 6,174,968, and 6,225,390, a butadiene segment, an isoprene segment, a polyvinyl segment for example alkyl poly(meth)acrylate, or polyvinyl alcohol or poly(vinyl acetate), a silicone segment as described in U.S. Pat. Nos. 5,468,477 and 5,725,882, or a combination thereof.

A diblock copolymer may be defined as being of type A-B wherein a rigid segment (A) is followed by a flexible segment (B).

A triblock copolymer may be defined as being of type A-B-A or as a combination of a rigid segment, a flexible segment and a rigid segment.

A multi-block or radial or star copolymer can comprise any kind of combination of rigid segments and flexible segments, provided that the characteristics of the rigid segments and of the flexible segments are preserved.

As examples of rigid segments of a block copolymer, mentions can be made of styrene, and as examples of flexible segments of a block copolymer, mentions can be made of ethylene, propylene, butylene, and a combination thereof.

The triblock copolymers, and for example those of the polystyrene/polyisoprene or polystyrene/polybutadiene type, suitable for application of the disclosure, can be those marketed under the reference name LUVITOL HSB by the company BASF. Non-limiting mentions can also ne made of triblock copolymers of the polystyrene/copoly(ethylene-propylene) or polystyrene/copoly(ethylene-butylene) type, such as those marketed under the reference name KRATON by the company SHELL CHEMICAL CO, or under the reference GELLED PERMETHYL 99 A by the company PENRECO. The triblock copolymers are used in some of the embodiments according to the disclosure.

As further examples of block copolymers that may be suitable for application of the present disclosure, mention can be made of the block copolymers marketed under the reference VERSAGEL by the company PENRECO, those marketed under the reference KRATON by the company SHELL and those marketed under the reference GEL BASE by the company BROOKS INDUSTRIES.

Among the polymeric thickeners for the fatty phase, exemplary thickeners are the polymers with at least one crystallizable sequence in the backbone.

The polymeric thickeners for the aqueous phase or the fatty phase can be used alone or mixed in all proportions.

For example, the polymeric thickener or thickeners are chosen from the aqueous-phase polymeric thickeners.

The polymeric thickener or thickeners is/are present in the ready-to-use composition according to the disclosure in an amount ranging from 0.01 to 10 wt. % and such as from 0.1 to 5 wt. % relative to the total weight of the composition.

The ready-to-use composition according to the disclosure comprises at least one dye precursor.

The at least one dye precursor can be chosen from oxidation bases and couplers.

The oxidation base or bases usable for the application of the disclosure are chosen from those known conventionally in oxidation dyeing, among which non-limiting mentions can be made of ortho- and para-phenylenediamines, double bases, ortho- and para-aminophenols, heterocyclic bases as well as acid addition salts thereof.

These oxidation bases can for example be cationic.

The para-phenylenediamines usable for the application of the disclosure can for example be chosen from the compounds of the following formula (XX) and acid addition salts thereof:

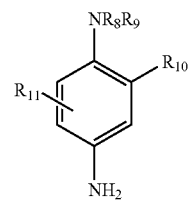

(XX)

wherein:

$R_8$ represents a hydrogen atom, a $C_1$-$C_4$ alkyl, $C_1$-$C_4$ monohydroxyalkyl, $C_2$-$C_4$ polyhydroxyalkyl, alkoxy($C_1$-$C_4$) alkyl($C_1$-$C_4$), $C_1$-$C_4$ alkyl radical substituted with a nitrogen-containing, phenyl or 4'-aminophenyl group;

$R_9$ represents a hydrogen atom, a $C_1$-$C_4$ alkyl, $C_1$-$C_4$ monohydroxyalkyl, $C_2$-$C_4$ polyhydroxyalkyl, alkoxy($C_1$-$C_4$) alkyl($C_1$-$C_4$) or $C_1$-$C_4$ alkyl radical substituted with a nitrogen-containing group;

$R_8$ and $R_9$ can also form, with the nitrogen atom bearing them, a nitrogen-containing heterocycle with 5 or 6 ring members optionally substituted with at least one group chosen from alkyl, hydroxyl and ureido;

$R_{10}$ represents a hydrogen atom, a halogen atom such as a chlorine atom, a $C_1$-$C_4$ alkyl, sulpho, carboxy, $C_1$-$C_4$ monohydroxyalkyl or $C_1$-$C_4$ hydroxyalkoxy, $C_1$-$C_4$ acetylaminoalkoxy, $C_1$-$C_4$ mesylaminoalkoxy or $C_1$-$C_4$ carbamoylaminoalkoxy radical;

$R_{11}$ represents a hydrogen atom, a halogen atom or a $C_1$-$C_4$ alkyl radical.

Among the nitrogen-containing groups of the above formula (XX), non-limiting mentions can be made of the amino, monoalkyl(C1-C4)amino, dialkyl(C1-C4)amino, trialkyl (C1-C4)amino, monohydroxyalkyl(C1-C4)amino, imidazolinium and ammonium radicals.

Among the para-phenylenediamines of the above formula (XX), non-limiting mentions can be made of para-phenylenediamine, para-toluoylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methyl-aniline, 4-N,N-bis-(β-hydroxyethyl)amino-2-methyl-aniline, N,N-bis-β-hydroxyethyl paraphenylenediamine, 4-N,N-bis-(β-hydroxyethyl)-amino-2-chloro-aniline, 2-β-hydroxyethyl-para-phenylenediamine, 2-fluoro-para-phenylenediamine, 2-isopropyl-para-phenylenediamine, N-β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β-dihydroxypropyl)-para-phenylenediamine, N-(β-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β- methoxyethyl)-para-phenylenediannine, 2-methyl-1-N-β-hydroxyethyl-para-phenylenediamine, and acid addition salts thereof.

Among the para-phenylenediamines of the above formula (XX), further non-limiting mentions can be made of para-phenylenediamine, para-toluoylenediamine, 2-isopropyl-para-phenylenediamine, 2-β-hydroxyethyl-para-phenylenediannine, 2,6-dimethyl-para-phenylenediamine, 2,6-diethyl-para-phenylenediamine, 2,3-dimethyl-para-phenylenediamine, 2-chloro-para-phenylenediamine, N,N-bis-β-hydroxyethyl paraphenylenediamine, and acid addition salts thereof.

For example, in some embodiments, para-phenylenediamine and para-toluoylenediamine, N,N-bis-β-hydroxyethyl paraphenylenediamine, and their salts of addition with an acid, can be used.

According to the disclosure, double bases may be compounds having at least two aromatic nuclei bearing amino and/or hydroxyl groups.

Among the double bases usable as oxidation bases in the ready-to-use composition according to the disclosure, non-limiting mention can be made of the compounds corresponding to the following formula (XXI) and acid addition salts thereof:

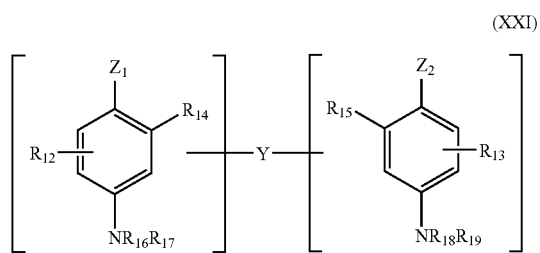

(XXI)

wherein:
$Z_1$ and $Z_2$, which may be identical or different, represent a hydroxyl or —$NH_2$ radical, which can be substituted with a $C_1$-$C_4$ alkyl radical or with a linkage Y;
the linkage Y represents a linear or branched alkylene chain having from 1 to 14 carbon atoms, which can be interrupted or terminated by at least one nitrogen-containing groups and/or by at least one heteroatom such as chosen from oxygen, sulphur and nitrogen atom, and optionally substituted with at least one hydroxyl or $C_1$-$C_6$ alkoxy radical;
$R_{12}$ and $R_{13}$, independently, represent a hydrogen or halogen atom, a $C_1$-$C_4$ alkyl, $C_1$-$C_4$ monohydroxyalkyl, $C_2$-$C_4$ polyhydroxyalkyl, $C_1$-$C_4$ alkylamino radical or a linkage Y;
$R_{14}$, $R_{15}$, $R_{16}$, $R_{17}$, $R_{18}$ and $R_{19}$, which may be identical or different, represent a hydrogen atom, a linkage Y or a $C_1$-$C_4$ alkyl radical;
provided that the compounds of formula (XXI) only have a single linkage Y per molecule.

Among the nitrogen-containing groups of the above formula (XXI), non-limiting mentions can be made of the amino, monoalkyl(C1-C4)amino, dialkyl(C1-C4)amino, trialkyl(C1-C4)amino, monohydroxyalkyl(C1-C4)amino, imidazolinium and ammonium radicals.

Among the double bases of the above formula (XXI), non-limiting mentions can be made of N,N'-bis-(β-hydroxyethyl)-N,N'-bis-(4'-aminophenyl)-1,3-diamino-propanol, N,N'-bis-(β-hydroxyethyl)-N,N'-bis-(4'-aminophenyl)-ethylenediamine, N,N'-bis-(4-aminophenyl)-tetramethylenediamine, N,N'-bis-β-hydroxyethyl)-N,N'-bis-(4-aminophenyl)-tetramethylenediamine, N,N'-bis-(4-methyl-aminophenyl)-tetramethylenediamine, N,N'-bis-(ethyl)-N,N'-bis-(4'-amino-3'-methylphenyl)-ethylenediamine, 1,8-bis-(2,5-diaminophenoxy)-3,5-dioxaoctane, and acid addition salts thereof.

Among these double bases of formula (XXI), further non-limiting mentions can be made of N,N'-bis-(β-hydroxyethyl)-N,N'-bis-(4'-aminophenyl)-1,3-diamino-propanol, 1,8-bis-(2,5-diaminophenoxy)-3,5-dioxaoctane or acid addition salts thereof.

The para-aminophenols usable for the application of the disclosure can for example be chosen from the compounds corresponding to the following formula (XXII) and acid addition salts thereof:

(XXII)

wherein:
$R_{20}$ represents a hydrogen atom, a halogen atom such as fluorine, a $C_1$-$C_4$ alkyl, $C_1$-$C_4$ monohydroxyalkyl, alkoxy($C_1$-$C_4$)alkyl($C_1$-$C_4$) or $C_1$-$C_4$ alkylamino, or $C_1$-$C_4$ hydroxyalkyl($C_1$-$C_4$) alkylamino radical;
$R_{21}$ represents a hydrogen atom or a halogen atom such as fluorine, a $C_1$-$C_4$ alkyl, $C_1$-$C_4$ monohydroxyalkyl, $C_2$-$C_4$ polyhydroxyalkyl, $C_1$-$C_4$ alkylamino, $C_1$-$C_4$ cyanoalkyl or alkoxy($C_1$-$C_4$)alkyl($C_1$-$C_4$) radical.

Among the para-aminophenols of the above formula (XXII), non-limiting mentions can be made of para-aminophenol, 4-amino-3-methylphenol, 4-amino-3-fluoro-phenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)-phenol, and acid addition salts thereof.

Further non-limiting mentions can be made of para-aminophenol and 4-amino-3-methylphenol.

The ortho-aminophenols usable as oxidation bases for the application of the present disclosure are for example chosen from 2-aminophenol, 2-amino-1-hydroxy-5-methylbenzene, 2-amino-1-hydroxy-6-methylbenzene, 5-acetamido-2-aminophenol, and acid addition salts thereof.

Among the heterocyclic bases usable as oxidation bases in the ready-to-use composition according to the disclosure, non-limiting mentions can be made of pyridine derivatives, pyrimidine derivatives, pyrazole derivatives, and acid addition salts thereof.

Among the pyridine derivatives, further non-limiting mentions can be made of the compounds described for example in Great Britain Patent Nos. 1 026 978 and 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and acid addition salts thereof.

Among the pyrimidine derivatives, further non-limiting mentions can be made of the compounds described for example in German Patent No. 2 359 399 or Japanese Patent Nos. 88-169 571 and 91-10659 or PCT Patent Application Publication No. WO 96/15765, such as 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and pyrazolopyrimidine derivatives such as those mentioned in French Patent Application Publication No. 2 750 048 and among which non-limiting mentions can be made of pyrazolo-[1,5-a]-pyrimidine-3,7-diamine; 2,5-dimethyl-pyrazolo-[1,5-a]-pyrimidine-3,7-diamine; pyrazolo-[1,5-a]-pyrimidine-3,5-diamine; 2,7-dimethyl-pyrazolo-[1,5-a]-pyrimidine-3,5-diamine; 3-amino-pyrazolo-[1,5-a]-pyrimidin-7-ol; 3-amino-pyrazolo-[1,5-a]-pyrimidin-5-ol; 2-(3-amino pyrazolo-[1,5-a]-pyrimidin-7-ylamino)-ethanol; 2-(7-amino-pyrazolo-[1,5-a]-pyrimidin-3-ylamino)-ethanol; 2-[(3-amino-pyrazolo[1,5-a]pyrimidin-7-yl)-(2-hydroxy-ethyl)-amino]-ethanol; 2-[(7-amino-pyrazolo[1,5-a]pyrimidin-3-yl)-(2-hydroxy-ethyl)-amino]-ethanol; 5,6-dimethyl-pyrazolo-[1,5-a]-pyrimidine-3,7-diamine; 2,6-dimethyl-pyrazolo-[1,5-a]-pyrimidine-3,7-diamine; 2,5,N7,N7-tetramethyl-pyrazolo-[1,5-a]-pyrimidine-3,7-diamine; 3-amino-5-methyl-7-imidazolylpropylamino-pyrazolo-[1,5-a]-pyrimidine; acid addition salts thereof and tautomeric forms thereof, when there is tautomeric equilibrium.

Among the pyrazole derivatives, further non-limiting mentions can be made of the compounds described in German Patent Nos. 3 843 892 and 4 133 957 and PCT Patent Application Publication Nos. WO 94/08969 and WO 94/08970, French Application Publication No. 2 733 749 and German Application Publication No. 195 43 988 such as 4,5-diaminopyrazoles, for example 4,5-diamino-1-methylpyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1(β-hydroxyethyl)-pyrazole, 4,5-diamino-1-ethyl-3-methylpyrazole, 4,5-diamino-1-ethyl-3-(4'-methoxyphenyl)-pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole and 4-amino-5-(2'-aminoethyl)amino-1,3-dimethylpyrazole; 3,4-diamino-pyrazole; 4-amino-1,3-dimethyl-5-hydrazino-pyrazole; 3,4,5-triaminopyrazoles, for example 3, 4,5-triamino-pyrazole, 1-methyl-3,4,5-triamino-pyrazole, 3,5-diamino-1-methyl-4-methylamino-pyrazole, 3,5-diamino-4-(β-hydroxyethyl)amino-1-methylpyrazole; and acid addition salts thereof.

Further non-limiting mention can be made of 4,5-diaminopyrazole, and such as 4,5-diamino-1-(β-hydroxyethyl)-pyrazole and/or a salt thereof.

As pyrazole derivatives, non-limiting mentions can be made of the diamino-N,N-dihydropyrazolopyrazolones and for example those described in French Application No. 2 886 136 such as the following compounds and addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[2-a]pyrazol-1-one, 4,5-diamino-1,2-dimethyl-1,2-dihydro-pyrazol-3-one, 4,5-diamino-1,2-diethyl-1,2-dihydro-pyrazol-3-one, 4,5-diamino-1,2-di-(2-hydroxyethyl)-1,2-dihydro-pyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydro-pyrazol-3-one, 4-amino-5-(3-dimethylamino-pyrrolidin-1-yl)-1,2-diethyl-1,2-dihydro-pyrazol-3-one, 2,3-diamino-6-hydroxy-6,7-dihydro-1H, and 5H-pyrazolo[1,2-a]pyrazol-1-one.

Even further non-limiting mentions can be made of 2,3-diamino-6,7-dihydro-1H,5H-pyrazolo[1,2-a]pyrazol-1-one and/or addition salts thereof.

As heterocyclic bases, further non-limiting mentions can be made of 4,5-diamino-1-(β-hydroxyethyl)pyrazole and/or 2,3-diamino-6,7-dihydro-1H,5H-pyrazolo[1,2-a]pyrazol-1-one and/or addition salts thereof.

As cationic oxidation bases usable in the ready-to-use compositions according to the disclosure, non-limiting mentions can be made of the following compounds: the para-phenylenediamines for example as described in French Patent Application Nos. 2 766 177 and 2 766 178, the para-aminophenols as described for example in French Patent Application Nos. 2 766 177 and 2 766 178, the ortho-phenylenediamines as described for example in French Patent Application Nos. 2 782 718, 2 782 716 and 2 782 719, the ortho-aminophenols or cationic double bases such as derivatives of the bis(aminophenyl)alkylenediamine type described in French Patent Application No. 2 766 179, as well as the cationic heterocyclic bases, the compounds bearing at least one quaternary nitrogen atom.

For example, the cationic oxidation bases usable in the compositions according to the disclosure are cationic para-phenylenediamines. For example, in some embodiments cationic oxidation bases of para-phenylenediamine structure can be used, wherein at least one of the amine functions is a tertiary amine bearing a pyrrolidine nucleus, the molecule possessing at least one quaternized nitrogen atom. Such bases are described, for example, in European Patent Application Publication No. 1 348 695.

The ready-to-use composition according to the disclosure for example comprises a total quantity of oxidation bases ranging from 0.0005 to 12 wt. % relative to the total weight of the ready-to-use composition. For example, it comprises a total quantity of oxidation bases in the range from 0.005 to 8 wt. %, and further such as from 0.05 to 5 wt. %, relative to the total weight of said composition.

The coupler or couplers usable in the composition according to the disclosure are those conventionally used in compositions for oxidation dyeing, i.e. meta-aminophenols, meta-phenylenediamines, metadiphenols, naphthols and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines, and acid addition salts thereof.

These couplers are for example chosen from 2,4-diamino-1-(β-hydroxyethyloxy)-benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis-(2,4-diaminophenoxy)-propane, sesamol, 1-amino-2-methoxy-4,5-methylenedioxy benzene, α-naphthol, 6-hydroxy-indole, 4-hydroxy-indole, 4-hydroxy-N-methyl indole, 6-hydroxy-indoline, 2,6-dihydroxy-4-methyl-pyridine, 1-H-3-methylpyrazol-5-one, 1-phenyl-3-methylpyrazol-5-one, 2-amino-3-hydroxypyridine, 3,6-dimethyl-pyrazolo-[3,2-c]-1,2,4-triazole, 2,6-dimethyl-pyrazolo-[1,5-b]-1,2,4-triazole and acid addition salts thereof.

The ready-to-use composition according to the disclosure generally comprises a total amount of couplers in the range from 0.0001 to 15 wt. % relative to the total weight of the ready-to-use composition. For example, it comprises a total amount of couplers ranging from 0.001 to 10 wt. %, and such as from 0.01 to 8 wt. %, relative to the total weight of the ready-to-use composition.

The oxidation bases and couplers can be present in the ready-to-use compositions of the disclosure in the form of addition salts, and for example in the form of acid addition salts.

The acid addition salts usable for the application of the disclosure are, for example, chosen from hydrochlorides, hydrobromides, sulphates, citrates, succinates, tartrates, lactates, acetates, alkylsulphates and alkylsulphonates.

When the oxidation bases or the couplers comprise at least one carboxylic or sulphonic acid function, base addition salts can be envisaged. The base addition salts usable for the dyeing compositions of the disclosure are then for example those obtained with sodium hydroxide, potassium hydroxide, and/or ammonia or amines.

According to at least one embodiment of the disclosure, the ready-to-use composition comprises at least one oxidation bases and at least one couplers.

According to at least one embodiment, the additional oxidation base is chosen from para-aminophenols, heterocyclic bases and the acid addition salts thereof.

The ready-to-use composition according to the present disclosure comprises at least one oxidizing agent.

The oxidizing agent is chosen for example from the peroxides such as hydrogen peroxide, urea peroxide, bromates and ferricyanides of alkali metals, the persalts such as perborates, percarbonates and persulphates. It is also possible to use, as oxidizing agents, at least one oxidation-reduction enzymes such as laccases, peroxidases and oxidoreductases with 2 electrons (such as uricase), optionally in the presence of their respective donor or cofactor.

The use of hydrogen peroxide is exemplified. This oxidizing agent for example comprises a solution of hydrogen peroxide whose strength can vary, such as, from about 1 to 40 volumes (i.e. about 0.3 to 12% of hydrogen peroxide), and further such as from about 5 to 40 volumes (i.e. about 1.5 to 12% of hydrogen peroxide).

The concentration of oxidizing agent(s) in the ready-to-use composition of the invention is for example ranging from 0.1 to 20% and such as from 0.5 to 10% relative to the total weight of the composition.

The ready-to-use composition of the disclosure comprises at least one alkaline agent wherein at least one of them is an organic amine. This or these alkaline agent(s) are for example chosen from ammonia, carbonates or bicarbonates of alkali metals, such as of sodium or of potassium, alkanolamines such as mono-, di- and triethanolamines as well as their derivatives, hydroxyalkylamines and ethoxylated and propoxylated ethylenediamines, hydroxides of sodium and of potassium, amino acids and such as basic amino acids such as arginine or lysine and compounds of the following formula (XXIII):

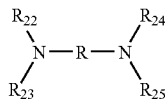

(XXIII)

wherein:
R is a propylene residue optionally substituted with a hydroxyl group or a $C_1$-$C_4$ alkyl radical;
$R_{22}$, $R_{23}$, $R_{24}$ and $R_{25}$, which may be identical or different, represent a hydrogen atom, a $C_1$-$C_4$ alkyl or $C_1$-$C_4$ hydroxyalkyl radical.

According to at least one embodiment, the ready-to-use composition comprises as alkaline agent at least one organic amine, such as at least one alkanolamine. When the ready-to-use composition comprises more than one alkaline agents including an alkanolamine and ammonium hydroxides or salts thereof, the amount of organic amine (s) are for example higher than the amount of ammonia.

According to at least one embodiment, the ready-to-use composition contains a small amount of ammonia, or even no ammonia. According to this embodiment, the ready-to-use composition for example contains at least one alkanolamine, such as monoethanolamine.

The concentration of alkaline agent(s) in the ready-to-use composition of the disclosure, for example, ranges from 0.01 to 30%, and such as from 0.1 to 20% by weight relative to the total weight of the ready-to-use composition.

The ready-to-use composition according to the disclosure can moreover comprise at least one direct dye, which can, for example, be chosen from the nitro dyes of the benzene series, the azo direct dyes, the methine direct dyes, and addition salts thereof. These direct dyes can be of non-ionic, anionic or cationic character.

The ready-to-use composition can also comprise other compounds constituting the coloring medium. This coloring medium may comprise water or a mixture of water and at least one acceptable organic solvent, such as water-soluble in the cosmetics area.

As examples of organic solvents, non-limiting mentions can be made of alcohols such as ethyl alcohol, isopropyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. The at least one solvent can then be present in an amount ranging from 0.01 to 35 wt. %, and such as from 0.1 to 25 wt. % relative to the total weight of the ready-to-use composition.

For example, in some embodiments the ready-to-use composition of the disclosure comprises water. As further examples, the concentration of water can range from 10 to 70%, and such as from 20 to 55% by weight relative to the total weight of the composition.

The ready-to-use composition according to the disclosure can also comprise at least one additive used conventionally in compositions for dyeing the hair.

"Additive" means a substance that is added, different from the compounds already mentioned.

As examples of additives that can be used, non-limiting mentions can be made of anionic, cationic, non-ionic, amphoteric, zwitterionic surfactants or mixtures thereof; anionic, cationic, non-ionic, amphoteric, zwitterionic polymers, mineral or organic, non-polymeric thickening agents; antioxidants or reducing agents; penetrating agents; sequestering agents; perfumes; buffers; dispersants; conditioners, such as for example volatile or non-volatile, modified or unmodified silicones; film-forming agents; ceramides; preservatives; opacifiers; and antistatic agents.

The above additives can be present in an amount, for each of them, ranging from 0.01 to 20 wt. % relative to the weight of the ready-to-use composition.

In some embodiments, the ready-to-use composition of the disclosure comprises at least one surfactant.

For example, the surfactant or surfactants are chosen from non-ionic surfactants and anionic surfactants.

The anionic surfactants, for example, can be chosen from the salts (for example salts of alkali metals, such as sodium, ammonium salts, salts of amines such as the salts of aminoalcohols or salts of alkaline-earth metals such as magnesium) of the following compounds:

alkylsulphates, alkyl ether sulphates, alkylamidoether sulphates, alkaryl-polyether sulphates, monoglyceride sulphates;

alkylsulphonates, alkylamidesulphonates, alkarylsulphonates, α-olefin-sulphonates, paraffin-sulphonates;

alkylphosphates, alkyl ether phosphates;

alkylsuiphosuccinates, alkyl ether sulphosuccinates, alkylamide-sulphosuccinates; alkylsulphosuccinamates;

alkylsulphoacetates;

acylsarcosinates; acylisethionates and N-acyltaurates;

salts of fatty acids such as oleic, ricinoleic, palmitic, stearic acids, acids of copra oil or of hydrogenated copra oil;

salts of alkyl-D-galactoside-uronic acids;

acyl-lactylates;

salts of polyalkoxylated alkyl ether carboxylic acids, polyalkoxylated alkaryl ether carboxylic acids, polyalkoxylated alkylamidoether carboxylic acids, such as those with from 2 to 50 ethylene oxide groups;

and mixtures thereof.

In some embodiments, the alkyl or acyl radical of these various compounds may have from 6 to 24 carbon atoms, and such as from 8 to 24 carbon atoms, with the aryl radical, for example, denoting a phenyl or benzyl group.

The non-ionic surfactants are for example chosen from the mono- or poly-alkoxylated, mono- or poly-glycerolated non-ionic surfactants. The alkoxylated units are for example ethoxylated or propoxylated units, or a combination thereof, for further example, ethoxylated.

As examples of alkoxylated non-ionic surfactants, non-limiting mentions can be made of:

alkoxylated alkyl($C_8$-$C_{24}$)phenols, saturated or unsaturated, linear or branched, alkoxylated $C_8$-$C_{30}$ alcohols, saturated or unsaturated, linear or branched, alkoxylated $C_8$-$C_{30}$ amides, esters of saturated or unsaturated, linear or branched $C_8$-$C_{30}$ acids, and of polyethylene glycols, esters of saturated or unsaturated, linear or branched $C_8$-$C_{30}$ acids, and of polyethoxylated sorbitol, ethoxylated, saturated or unsaturated vegetable oils, condensates of ethylene oxide and/or of propylene oxide, among others, alone or mixed.

The surfactants may have a number of moles of ethylene oxide and/or propylene oxide ranging from 1 to 50, such as from 2 to 30. As further examples, the non-ionic surfactants do not comprise propoxylated units.

According to at least one embodiment of the disclosure, the alkoxylated non-ionic surfactants are chosen from the ethoxylated $C_8$-$C_{30}$, such as ethoxylated $C_{18}$-$C_{30}$, alcohols.

As examples of mono- or poly-glycerolated non-ionic surfactants, mentions can be made of the mono- or poly-glycerolated $C_8$-$C_{40}$ alcohols.

For example, the mono- or poly-glycerolated $C_8$-$C_{40}$ alcohols correspond to the following formula:

$$RO-[CH_2-CH(CH_2OH)-O]_m-H$$

wherein R represents a linear or branched, $C_8$-$C_{40}$, such as $C_8$-$C_{30}$ alkyl or alkenyl radical, and m represents a number ranging from 1 to 30 and such as from 1 to 10.

As examples of compounds suitable for the application of the disclosure, mentions can be made of lauric alcohol with 4 moles of glycerol (INCI name: POLYGLYCERYL-4 LAURYL ETHER), lauric alcohol with 1.5 moles of glycerol, oleic alcohol with 4 moles of glycerol (INCI name: POLYGLYCERYL-4 OLEYL ETHER), oleic alcohol with 2 moles of glycerol (INCI name: POLYGLYCERYL-2 OLEYL ETHER), cetearyl alcohol with 2 moles of glycerol, cetearyl alcohol with 6 moles of glycerol, oleocetyl alcohol with 6 moles of glycerol, and octadecanol with 6 moles of glycerol.

The alcohol can represent a mixture of alcohols and the value of m represents a statistical value, which signifies that a commercial product can comprise several species of polyglycerolated fatty alcohols in the form of a mixture.

Among the mono- or poly-glycerolated alcohols, mentions can be made of $C_8$/$C_{10}$ alcohol with one mole of glycerol, $C_{10}$/$C_{12}$ alcohol with 1 mole of glycerol and $C_{12}$ alcohol with 1.5 mole of glycerol.

For example, in some embodiments the surfactant present in the ready-to-use composition of the disclosure is a non-ionic surfactant.

The content of surfactants in the ready-to-use composition of the disclosure, for example, ranges from 0.1 to 50 wt. %, such as from 0.5 to 30 wt. % relative to the total weight of the ready-to-use composition.

Of course, a person skilled in the art will take care to choose the optional additive(s) mentioned previously, in such a way that the expected properties attached intrinsically to the ready-to-use compositions according to the disclosure are not, or substantially are not, adversely affected by the addition (or additions) considered.

The pH of the ready-to-use composition according to the disclosure can range from 3 to 12, such as from 5 to 11, further such as from 7 to 11. It can be adjusted to the desired value by means of acidifying or alkalizing agents usually employed in the dyeing of keratin fibers or else by means of conventional buffer systems.

The alkaline agents are for example those described previously.

Among the acidifying agents, mentions can be made of, for example, mineral or organic acids such as hydrochloric acid, orthophosphoric acid, carboxylic acids such as tartaric acid, citric acid, lactic acid, or sulphonic acids.

The ready-to-use composition according to the disclosure can be in various forms, such as in the form of liquids, creams, gels, or in any other suitable form for carrying out dyeing of keratin fibers, and such as of human hair.

The method of the present disclosure is a method comprising applying the ready-to-use composition according to the present disclosure as defined previously to the keratin fibers. The color can be developed at acid, neutral or alkaline pH and the oxidant can be added at the moment of use or it can be used simultaneously or sequentially with the other compounds of the ready-to-use composition of the disclosure.

After a resting time on the keratin fibers, for example, ranging from about 1 to 60 minutes, such as from about 5 to 45 minutes, the keratin fibers are rinsed, optionally washed with shampoo and rinsed again, then dried.

The ready-to-use compositions according to the disclosure can result from mixing at least two compositions and for example 2 or 3 compositions, for example including an oxidizing composition comprising at least one oxidant as defined previously. The ready-to-use compositions can be obtained before application to the keratin fibers, or simultaneously with application to the keratin fibers, One of the compositions can be anhydrous.

Provided is also a multi-compartment kit, comprising:

a first compartment comprising at least one fatty substance other than fatty acids, a second compartment comprising at least one dye precursor and optionally at least one alkaline agent, and a third compartment comprising at least one oxidizing agent, and optionally at least one fatty substance other than fatty acids, and wherein at least one of the three compartments further comprises at least one polymeric thickener.

In some embodiments, the composition comprising the fatty substances can be anhydrous. Anhydrous composition means, in the sense of the disclosure, a cosmetic composition having a water content below 5 wt. %, such as below 2 wt. % and further such as below 1 wt. % relative to the weight of said composition. It should be noted that this refers for example to bound water, such as the water of crystallization of the salts or traces of water absorbed by the raw materials used in the preparation of the compositions according to the disclosure. For example, the polymeric thickener or thickeners are contained in the second or third compartments and such as in the second compartment.

Also provided is a multi-compartment kit comprising:

a first compartment comprising at least one fatty substance other than fatty acids and at least one oxidizing agent, and a second compartment comprising at least one dye precursor and optionally at least one alkaline agent, wherein at least one of the first and second compartments, for example, the second compartment, further comprises at least one polymeric thickener.

Further provided is a multi-compartment kit comprising:

a first compartment comprising at least one fatty substance other than fatty acids, at least one dye precursor, and optionally at least one alkaline agent, and a second compartment comprising at least one oxidizing agent, wherein at least one of the first and second compartments, such as the second compartment, further comprises at least one polymeric thickener.

These kits can be equipped with at least one of applicators for delivery of the desired mixture onto the hair, such as the applicators described in French Patent No. 2 586 913.

The examples given below are intended to illustrate the invention but without limiting the scope thereof.

EXAMPLES

The following compositions were prepared (concentrations stated for the products as they were):

Example 1

| Composition 1 | Concentration (g %) |
|---|---|
| DISTEARDIMONIUM HECTORITE | 3 |
| OCTYLDODECANOL | 11.5 |
| GLYCOL DISTEARATE | 8 |

-continued

| Composition 1 | Concentration (g %) |
|---|---|
| LIQUID PARAFFIN | 64.5 |
| PROPYLENE CARBONATE | 1 |
| LAURETH-2 | 1 |
| POLYSORBATE 21 | 11 |

| Composition 2 | concentration (g %) |
|---|---|
| DIETHYLENETRIAMINE PENTAACETIC ACID, PENTASODIUM SALT IN AQUEOUS SOLUTION AT 40% | 1 |
| SODIUM METABISULPHITE | 0.7 |
| MONOETHANOLAMINE | 14.5 |
| 1-METHYL-2,5-DIAMINOBENZENE | 2.25 |
| 2,4-DIAMINOPHENOXYETHANOL HCl | 0.05 |
| 1,3-DIHYDROXYBENZENE (RESORCINOL) | 2 |
| m-AMINOPHENOL | 0.36 |
| NATROSOL 250 HHR (hydroxyethylcellulose) | 1.5 |
| HEXYLENE GLYCOL | 3 |
| DIPROPYLENE GLYCOL | 3 |
| ETHYL ALCOHOL | 8.25 |
| PROPYLENE GLYCOL | 6.2 |
| ASCORBIC ACID | 0.25 |
| WATER | Qs 100 g |

| Composition 3 | Concentration (g %) |
|---|---|
| DIETHYLENETRIAMINE PENTAACETIC ACID, PENTASODIUM SALT IN AQUEOUS SOLUTION AT 40% | 0.15 |
| HYDROGEN PEROXIDE IN SOLUTION AT 50% (HYDROGEN PEROXIDE 200 VOL.) | 12 |
| SODIUM STANNATE | 0.04 |
| SODIUM PYROPHOSPHATE | 0.03 |
| LIQUID PARAFFIN | 20 |
| HEXADIMETHRINE CHLORIDE (AS at 60% in water) | 0.25 |
| POLYQUATERNIUM-6 (AS at 40% in water) | 0.5 |
| GLYCEROL | 0.5 |
| CETYLSTEARYL ALCOHOL ($C_{16}/C_{18}$ 30/70) | 8 |
| ETHOXYLATED CETYLSTEARYL ALCOHOL (33 EO) | 3 |
| ETHOXYLATED AMIDE OF COLZA ACIDS (4 EO) PROTECTED at 92.3% in water | 1.3 |
| VITAMIN E | 0.1 |
| PHOSPHORIC ACID | Qs pH 2.2 |
| WATER | QS 100 g |

Example 2

| Composition 2' | concentration (g %) |
|---|---|
| DIETHYLENETRIAMINE PENTAACETIC ACID, PENTASODIUM SALT IN AQUEOUS SOLUTION AT 40% | 1 |
| SODIUM METABISULPHITE | 0.7 |
| MONOETHANOLAMINE | 14.5 |
| 1-METHYL-2,5-DIAMINOBENZENE | 2.25 |

-continued

| Composition 2' | concentration (g %) |
|---|---|
| 2,4-DIAMINOPHENOXYETHANOL HCl | 0.05 |
| 1,3-DIHYDROXYBENZENE (RESORCINOL) | 2 |
| m-AMINOPHENOL | 0.36 |
| NATROSOL PLUS 330 CS cetylhydroxyethylcellulose) | 2 |
| DIPROPYLENE GLYCOL | 3 |
| HEXYLENE GLYCOL | 3 |
| PROPYLENE GLYCOL | 6.2 |
| ASCORBIC ACID | 0.25 |
| WATER | Qs 100 g |

Compositions 1' and 3' employed in Example 2 were identical, respectively, to compositions 1 and 3 described in example 1.

Example 3

| Composition 1" | Concentration (g %) |
|---|---|
| OCTYLDODECANOL | 14.5 |
| INTELIMER IPA 13-6 | 5 |
| LIQUID PARAFFIN | 74 |
| OLETH-10 | 6.5 |

Compositions 2" and 3" employed in Example 3 were identical, respectively, to compositions 2 and 3 described in Example 1.

Compositions 1, 2, 3 (for Example 1), and 1', 2' and 3' (for Example 2), and 1", 2", 3" (for Example 3), were mixed at the moment of use in the following proportions: 10 g of composition 1 (or 1' or 1") with 4 g of composition 2 (or 2' or 2") and 16 g of composition 3 (or 3' or 3"). The mixture was applied on locks of natural grey hair at 90% of white hair at a rate of 10 g of mixture to 1 g of hair. After waiting 30 minutes, the hair was rinsed, washed with a standard shampoo and dried.

The hair coloring was assessed visually.

| Example 1 | Light chestnut Natural |
|---|---|
| Example 2 | Light chestnut Natural |
| Example 3 | Light chestnut Natural |

What is claimed is:

1. A ready-to-use composition for the oxidation dyeing of keratin fibers, comprising:
   A) at least one fatty substance other than fatty acids present in the ready-to-use composition in an amount of greater than or equal to 25% by weight relative to the total weight of the ready-to-use composition,
   B) at least one polymeric thickener,
   C) at least one dye precursor,
   D) at least one oxidizing agent, and
   E) at least one alkaline agent wherein at least one of the at least one alkaline agent is an organic amine.

2. The ready-to-use composition according to claim 1, wherein the at least one fatty substance other than fatty acids is chosen from lower alkanes, fatty alcohols, esters of fatty acids, esters of fatty alcohol, non-silicone oils, non-silicone waxes and silicones.

3. The ready-to-use composition according to claim 1, wherein the at least one fatty substance other than fatty acids is non-silicone.

4. The ready-to-use composition according to claim 1, wherein the at least one polymeric thickener is a polymeric thickener for an aqueous phase.

5. The ready-to-use composition according to claim 1, wherein the at least one polymeric thickener is chosen from polymers with associative or non-associative sugar units, associative or non-associative acrylic or methacrylic anionic polymers, and associative or non-associative polyurethanes.

6. The ready-to-use composition according to claim 1, wherein the at least one polymeric thickener is a polymeric thickener for an oil phase.

7. The ready-to-use composition according to claim 1, wherein the at least one polymeric thickener is chosen from polymers having at least one crystallizable sequence in their backbone, non-siliconized polyamides, siliconized polyamides, mono- or polyalkyl esters of saccharide or polysaccharide, amide derivatives of N-acylated amino acids and copolymers comprising an alkylene or styrene sequence.

8. The ready-to-use composition according to claim 7, wherein the at least one polymeric thickener is chosen from polymers having at least one crystallizable sequence in their backbone.

9. The ready-to-use composition according to claim 1, wherein the at least one polymeric thickener is present in the ready-to-use composition in an amount ranging from 0.01 to 10 wt. % relative to the total weight of the composition.

10. The ready-to-use composition according to claim 9, wherein the at least one polymeric thickener is present in the ready-to-use composition in an amount ranging from 0.1 to 5 wt. % relative to the total weight of the composition.

11. The ready-to-use composition according to claim 1, wherein the at least one dye precursor is chosen from oxidation bases and couplers.

12. The ready-to-use composition according to claim 11, wherein the at least one dye precursor is chosen from ortho- and para-phenylenediamine oxidation bases, double bases, ortho- and para-aminophenols, heterocyclic bases, as well as salts of addition of these compounds with an acid and meta-aminophenol, meta-phenylenediamine, meta-diphenol, naphthol couplers, heterocyclic couplers and acid salts thereof.

13. The ready-to-use composition according to the claim 12, wherein the at least one dye precursor is chosen from aminophenols and meta-phenylenediamines.

14. The ready-to-use composition according to claim 1, wherein the at least one oxidizing agent is a peroxide.

15. The ready-to-use composition according to claim 14 wherein the at least one oxidizing agent is hydrogen peroxide.

16. The ready-to-use composition according to claim 1, wherein the at least one alkaline agent is chosen from ammonia and alkanolamine.

17. The ready-to-use composition according to claim 16, wherein the at least one alkaline agent is alkanolamine.

18. The ready-to-use composition according to claim 1, wherein the at least one alkaline agent is monoethanolamine.

19. A method of dyeing keratin fibers, comprising
   applying to the keratin fibers for a sufficient time to develop the desired coloration, a ready-to-use composition, wherein the ready-to-use composition comprises A) at least one fatty substance other than fatty acids present in the ready-to-use composition in an amount of greater than or equal to 25% by weight relative to the total weight of the ready-to-use composition,
B) at least one polymeric thickener,
C) at least one dye precursor,
D) at least one oxidizing agent, and
E) at least one alkaline agent wherein at least one of the at least one alkaline agent is an organic amine;
and wherein the ready-to-use composition can be formed before application to the keratin fibers.

20. A multi-compartment kit comprising
a first compartment comprising at least one fatty substance other than fatty acids,
a second compartment comprising at least one dye precursor, and at least one alkaline agent, and
a third compartment comprising at least one oxidizing agent, and optionally at least one fatty substance other than fatty acids,
and wherein at least one of the three compartments further comprises at least one polymeric thickener.

21. A multi-compartment kit comprising
a first compartment comprising at least one fatty substance other than fatty acids and at least one oxidizing agent, and
a second compartment comprising at least one dye precursor and at least one alkaline agent,
wherein at least one of the first and second compartments further comprises at least one polymeric thickener.

22. The multi-compartment kit according to claim 21, wherein the second compartment further comprises the at least one polymeric thickener.

23. A multi-compartment kit comprising
a first compartment comprising at least one fatty substance other than fatty acids, at least one dye precursor, at least one alkaline agent, and
a second compartment comprising at least one oxidizing agent,
wherein at least one of the first and second compartments further comprises at least one polymeric thickener.

24. The multi-compartment kit according to claim 23, wherein the second compartment further comprises at least one polymeric thickeners.

* * * * *